United States Patent
Fu et al.

(10) Patent No.: US 12,351,875 B2
(45) Date of Patent: Jul. 8, 2025

(54) DETECTING CANCER DRIVER GENES AND PATHWAYS

(71) Applicant: Roche Sequencing Solutions, Inc., Pleasanton, CA (US)

(72) Inventors: Yao Fu, San Mateo, CA (US); Aparna Chhibber, San Mateo, CA (US); Marghoob Mohiyuddin, Foster City, CA (US); Li Tai Fang, San Francisco, CA (US); Hugo Y. K. Lam, Sunnyvale, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1659 days.

(21) Appl. No.: 16/093,588

(22) PCT Filed: Apr. 14, 2017

(86) PCT No.: PCT/US2017/027794
§ 371 (c)(1),
(2) Date: Oct. 12, 2018

(87) PCT Pub. No.: WO2017/181134
PCT Pub. Date: Oct. 19, 2017

(65) Prior Publication Data
US 2021/0222248 A1 Jul. 22, 2021

Related U.S. Application Data

(60) Provisional application No. 62/323,535, filed on Apr. 15, 2016.

(51) Int. Cl.
*C12Q 1/6886* (2018.01)
*G16B 20/20* (2019.01)

(52) U.S. Cl.
CPC ........... *C12Q 1/6886* (2013.01); *G16B 20/20* (2019.02); *C12Q 2600/156* (2013.01)

(58) Field of Classification Search
None
See application file for complete search history.

(56) References Cited

FOREIGN PATENT DOCUMENTS

| CN | 103305625 A | 9/2013 |
|----|-------------|--------|
| KR | 2015-0102468 A | 9/2015 |

OTHER PUBLICATIONS

Lakshmanan et al Mucins in Lung Cancer: Diagnostic, Prognostic, and Therapeutic Implications Journal of Thoracic Oncology, vol. 10, Issue 1, Jan. 2015, pp. 19-27.*
Youn et al: "Identifying cancer driver genes in tumor genome sequencing studies", Bioinformatics, vol. 27, No. 2, Dec. 17, 2010 (Dec. 17, 2010), pp. 175-181, DOI: 10.1093/bioinformatics/btq630.*
Tokheim et al: "Evaluating the evaluation of cancer driver genes",Proceedings National Academy of Sciences PNAS, vol. 113, No. 50, Nov. 22, 2016 (Nov. 22, 2016), pp. 14330-14335, DOI: 10.1073/pnas. 1616440113.*
Korthauer et al: "MADGiC: a model-based approach for identifying driver genes in cancer", Bioinformatics, vol. 31, No. 10, May 15, 2015 (May 15, 2015), pp. 1526-1535, DOI: 10.1093/bioinformatics/btu858.*
Xiao et al: "Role of MUC20 overexpression as a predictor of recurrence and poor outcome in colorectal cancer", Journal of Translational Medicine, Biomed Central, vol. 11, No. 1, Jun. 20, 2013 (Jun. 20, 2013), p. 151, XP021155521, DOI: 10.1186/1479-5876-11-151.*
Korthauer, K.D. et al.; "MADGiC: a model-based approach for identifying driver genes in cancer"; *Bioinformatics*; vol. 31, No. 10; May 15, 2015; pp. 1526-1535.
Tokheim, C.J. et al.; "Evaluating the evaluation of cancer driver genes"; *Proceedings of National Academy of Sciences*; vol. 113, No. 50; Nov. 22, 2016; pp. 14330-14335.
Xiao, X. et al.; "Role of MUC20 overexpression as a predictor of recurrence and poor outcome in colorectal cancer"; *Journal of Translational Medicine*; Biomed Central Ltd.; vol. 11, No. 1; Jun. 20, 2013; pp. 151-162.
Youn, A. et al.; "Identifying cancer driver genes in tumor genome sequencing studies"; *Bioinformatics*; vol. 27, No. 2; Dec. 17, 2010; pp. 175-181.

* cited by examiner

*Primary Examiner* — Joseph Woitach
(74) *Attorney, Agent, or Firm* — Kilpatrick Townsend and Stockton LLP

(57) ABSTRACT

Described herein are methods, systems, and apparatuses for detecting significantly mutated genes/pathways in a cancer cohort. A driver gene detection technique taking into account the heterogeneous mutational context in a cancer cohort is disclosed. A statistical model of a gene-specific mutation rate distribution (e.g., using an optimized gene specific mean estimation and/or a gene-specific dispersion estimation) is used to model a sample/gene-specific background mutation rate. The statistical model may then be used to detect gene/pathway enrichment and distinguish tumor suppressors and oncogenes based on the spatial distribution of non-silent mutations, loss-of-function mutations, and/or gain-of-function mutations.

16 Claims, 17 Drawing Sheets

500

```
┌─────────────────────────────────────────────────────────────────────┐
│ Receive, for each sample of a plurality of samples from different   │
│ subjects having a same type of cancer, a set of mutations in DNA    │  510
│ measured in the sample, the DNA including a plurality of genes      │
└─────────────────────────────────────────────────────────────────────┘
                                    ↓
┌─────────────────────────────────────────────────────────────────────┐
│ For each sample of the plurality of samples, determine a sample     │
│ mutation rate ($b_s$) based on a total number of mutations          │  520
│ measured in the sample                                              │
└─────────────────────────────────────────────────────────────────────┘
                                    ↓
┌─────────────────────────────────────────────────────────────────────┐
│ For each mutation context of a plurality of mutation contexts,      │
│ determine a context mutation rate ($m_i$) based on a first number   │
│ of mutations identified in the sets of mutations for the mutation   │  530
│ context, wherein a mutation context corresponds to a type of        │
│ substitution or deletion                                            │
└─────────────────────────────────────────────────────────────────────┘
                                    ↓
┌─────────────────────────────────────────────────────────────────────┐
│ For each gene of the plurality of genes, determine an expected      │
│ silent mutation rate ($E_{g(silent)}$) using a sum of context       │
│ mutation rates of silent mutations in the gene, wherein a silent    │  540
│ mutation does not cause a change to an amino acid sequence of a     │
│ translated protein for the gene                                     │
└─────────────────────────────────────────────────────────────────────┘
                                    ↓
┌─────────────────────────────────────────────────────────────────────┐
│ For each gene of the plurality of genes, determine a probability    │
│ distribution of a gene-specific background mutation rate across     │
│ the plurality of samples for the gene, based on the expected        │  550
│ silent mutation rate for the gene and the sample mutation rate      │
│ for each sample                                                     │
└─────────────────────────────────────────────────────────────────────┘
                                    ↓
┌─────────────────────────────────────────────────────────────────────┐
│ Determine, for each gene of the plurality of genes, a measured      │
│ number of samples having at least one non-silent mutation in the    │  560
│ sets of mutations                                                   │
└─────────────────────────────────────────────────────────────────────┘
                                    ↓
┌─────────────────────────────────────────────────────────────────────┐
│ Determine, for each gene of the plurality of genes, an expected     │
│ number of samples having at least one non-silent mutation, based    │  570
│ on the probability distribution of the gene-specific background     │
│ mutation rate for the gene                                          │
└─────────────────────────────────────────────────────────────────────┘
                                    ↓
┌─────────────────────────────────────────────────────────────────────┐
│ Identify a group of genes having the measured number of samples     │
│ higher than the expected number of samples having at least one      │  580
│ non-silent mutation as candidate driver genes                       │
└─────────────────────────────────────────────────────────────────────┘
```

FIG. 5

| BRCA | LUAD | GBM | COAD |
|---|---|---|---|
| • MAPK signaling pathway<br>• Rap1 signaling pathway<br>• HIF-1 signaling pathway<br>• Phosphatidylinositol signaling system<br>• p53 signaling pathway<br>• PI3K-Akt signaling pathway<br>• AMPK signaling pathway<br>• VEGF signaling pathway<br>• ErbB signaling pathway<br>• TNF signaling pathway<br>• FoxO signaling pathway<br>• Phospholipase D signaling pathway<br>• Cell cycle<br>• mTOR signaling pathway<br>• cGMP-PKG signaling pathway<br>• Inositol phosphate metabolism<br>• Apoptosis<br>• cAMP signaling pathway<br>• Sphingolipid signaling pathway<br>• Signaling pathways regulating pluripotency of stem cells<br>• Jak-STAT signaling pathway<br>• Ras signaling pathway<br>• Wnt signaling pathway<br>• Focal adhesion<br>• Regulation of actin cytoskeleton | • ErbB signaling pathway<br>• Sphingolipid signaling pathway<br>• FoxO signaling pathway<br>• p53 signaling pathway<br>• Apoptosis<br>• Gap junction<br>• Regulation of actin cytoskeleton<br>• VEGF signaling pathway<br>• MAPK signaling pathway<br>• Phospholipase D signaling pathway<br>• Ras signaling pathway<br>• Signaling pathways regulating pluripotency of stem cells<br>• Rap1 signaling pathway<br>• PI3K-Akt signaling pathway<br>• mTOR signaling pathway<br>• HIF-1 signaling pathway<br>• Adherens junction | • p53 signaling pathway<br>• mTOR signaling pathway<br>• FoxO signaling pathway<br>• Sphingolipid signaling pathway<br>• Phosphatidylinositol signaling system<br>• Apoptosis<br>• Inositol phosphate metabolism<br>• ErbB signaling pathway<br>• HIF-1 signaling pathway | • Cell cycle<br>• VEGF signaling pathway<br>• Hippo signaling pathway<br>• Signaling pathways regulating pluripotency of stem cells<br>• Wnt signaling pathway<br>• Sphingolipid signaling pathway<br>• p53 signaling pathway<br>• Apoptosis<br>• Regulation of actin cytoskeleton<br>• ErbB signaling pathway<br>• FoxO signaling pathway<br>• MAPK signaling pathway<br>• mTOR signaling pathway<br>• Gap junction |

FIG. 11

| KEGG | MetaCyc | Reactome | PID |
|---|---|---|---|
| • MAPK signaling pathway<br>• Rap1 signaling pathway<br>• HIF-1 signaling pathway<br>• Phosphatidylinositol signaling system<br>• p53 signaling pathway<br>• PI3K-Akt signaling pathway<br>• AMPK signaling pathway<br>• VEGF signaling pathway<br>• ErbB signaling pathway<br>• TNF signaling pathway<br>• FoxO signaling pathway<br>• Phospholipase D signaling pathway<br>• Cell cycle<br>• mTOR signaling pathway<br>• cGMP-PKG signaling pathway<br>• Inositol phosphate metabolism<br>• Apoptosis<br>• cAMP signaling pathway<br>• Sphingolipid signaling pathway<br>• Signaling pathways regulating pluripotency of stem cells<br>• Jak-STAT signaling pathway<br>• Ras signaling pathway<br>• Wnt signaling pathway<br>• Focal adhesion<br>• Regulation of actin cytoskeleton | • 3-phosphoinositide biosynthesis<br>• Superpathway of inositol phosphate compounds | • Signaling by FGFR4 in disease<br>• Transcriptional activation of p53 responsive genes<br>• Transcriptional activation of cell cycle inhibitor p21<br>• Signaling by FGFR3 fusions in cancer<br>• Regulation of TP53 Expression<br>• Activation of NOXA and translocation to mitochondria | • IL6-mediated signaling events<br>• Atypical NF-kappaB pathway<br>• Signaling events mediated by the Hedgehog family<br>• Osteopontin-mediated events<br>• E-cadherin signaling in the nascent adherens junction<br>• p75(NTR)-mediated signaling<br>• BCR signaling pathway<br>• FAS (CD95) signaling pathway<br>• TRAIL signaling pathway<br>• Nephrin/Neph1 signaling in the kidney podocyte<br>• E-cadherin signaling in keratinocytes<br>• Signaling events mediated by Hepatocyte Growth Factor Receptor (c-Met)<br>• IFN-gamma pathway<br>• PLK3 signaling events<br>• Nongenotropic Androgen signaling<br>• Fc-epsilon receptor I signaling in mast cells<br>• VEGFR3 signaling in lymphatic endothelium<br>• CDC42 signaling events<br>• a6b1 and a6b4 Integrin signaling<br>• Ephrin B reverse signaling<br>• Nectin adhesion pathway |

FIG. 12 ial system,

DETECTING CANCER DRIVER GENES AND PATHWAYS

CROSS-REFERENCE TO RELATED APPLICATIONS

This application is a national phase application under 35 U.S.C. 371 claiming priority to PCT/US2017/027794, filed Apr. 14, 2017, which claims the benefit of U.S. Provisional Patent Application No. 62/323,535, filed on Apr. 15, 2016, the content of each of which is incorporated herein by reference in its entirety for all purposes.

BACKGROUND

The past decade has seen a large-scale application of next-generation sequencing technologies (NGS) in cancer genomics, and millions of somatic mutations have been discovered. The majority of somatic mutations are passenger mutations which accumulate during cancer progression, whereas a small portion of them (called drivers) are under positive selection, due to their contribution to tumorigenesis. Current methods utilize the following signs of positive selection to detect potential drivers: genes that are recurrently mutated across samples, genes that have spatial mutational pattern of inactivation or clustering, and genes that show functional impact bias. However, the low concordance across methods raises concerns about false positives and negatives in those findings.

BRIEF SUMMARY

Disclosed herein are techniques for identifying driver genes, mutations, and/or pathways for various types of cancer. For example, the identified driver genes may be used for diagnosis by identifying mutations occurring on the identified driver genes, or for treatment by targeting the identified driver genes.

In some embodiments, a driver gene may be identified by determining a gene-specific background mutation rate. In some embodiments, a statistical model for gene-specific background mutation rate may be determined by optimizing parameters estimated from single-gene and cross-genes modeling. In one example, the gene-specific background mutation can be statistically determined by recursively optimizing a gene-specific mean and a gene-specific dispersion using negative binomial regression and Bayesian inference. Genes, mutations, and/or pathways that have significantly more mutations than the expected background mutations across samples may be identified as candidate driver genes, mutations, and/or pathways.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The detailed description is set forth with reference to the accompanying figures.

FIG. 5 is a flow chart illustrating an example flow of detecting cancer driver genes, according to certain aspects of this disclosure.

FIG. 11 illustrates pathway enrichment across 4 tumor types.

FIG. 12 illustrates pathway enrichment in breast cancer cohort (BRCA) using different pathway datasets.

FIG. 14A illustrates the average number of somatic mutations per Mb in the exome per sample. FIG. 14B illustrates the intersection of the top 20 genes from ICGC and TCGA. FIG. 14C illustrates the gene rank (by p-values) of non-overlapping genes shown in FIG. 14B in the opposite dataset.

TERMS

Figure 1:
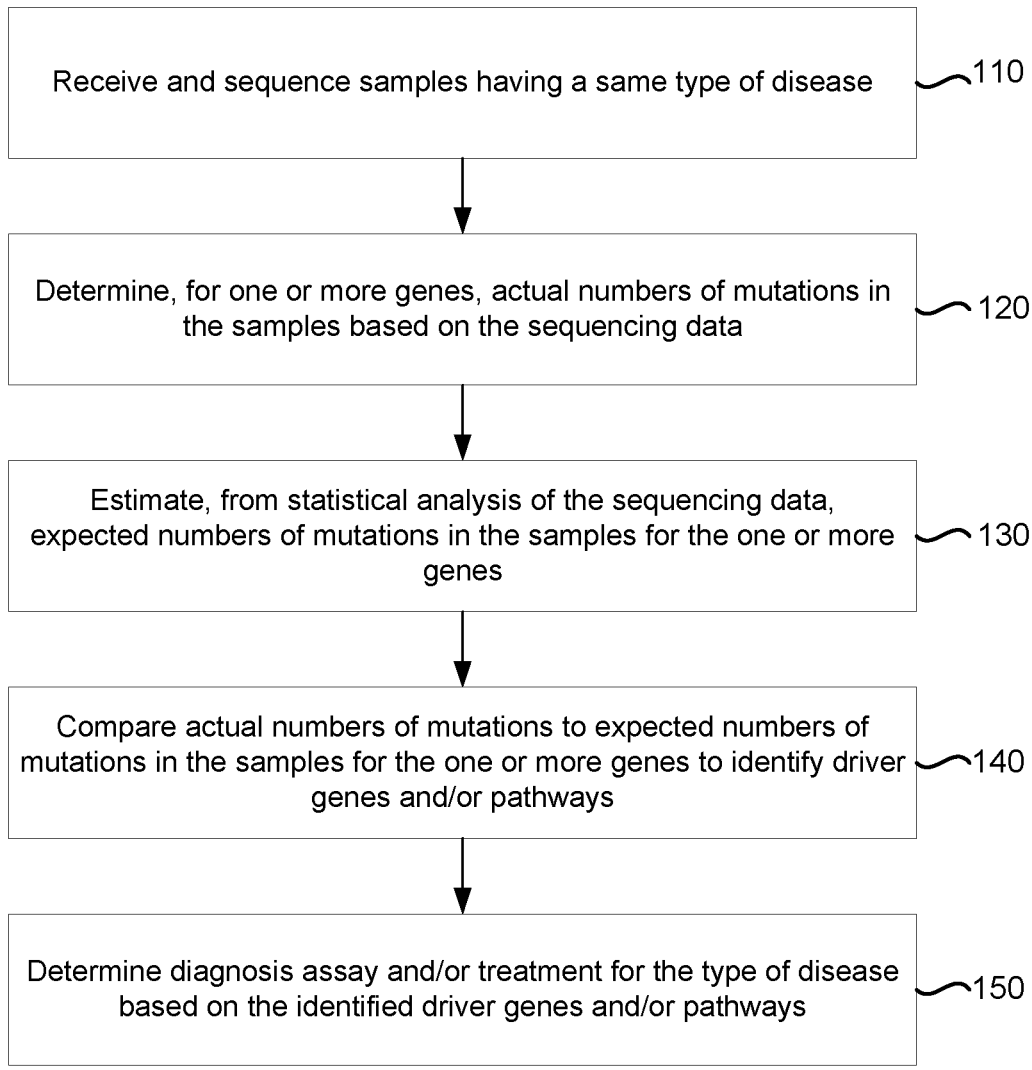
FIG. 1 is a flow chart illustrating an example method of detecting driver genes and pathways for diagnosis and treatment, according to certain aspects of this disclosure.

Mutations may be classified as silent or non-silent based on whether they cause a change to the amino acid sequence of the translated protein. As used herein, a silent mutation refers to a mutation that does not cause a change to an amino acid sequence of a translated protein for the gene, and a non-silent mutation refers to a mutation that causes a change to the amino acid sequence of the translated protein. Driver mutations are mutations that occur more frequently in a given cancer and are known to be involved in tumorigenesis.

For each gene, the possible mutations may include the tri-nucleotide mutation contexts (including 6 possible type of single base substitutions—C/G>A/T, C/G>G/C, C/G>T/A, T/A>A/T, T/A>C/G, T/A>G/C—and possible nucleotide contexts around each single base substitution) and indel mutation contexts. For example, the possible mutations may include a total of 97 mutation contexts (96 tri-nucleotide contexts and an indel mutation context). Since the substitution of A to C is the same as T to G, the number of possible types of substitutions is 6. Then, 4 options for each neighbor positions, provides 6×4×4=96 possible tri-nucleotide contexts.

Sample mutation rate may be used to represent the total mutation burden of a sample s. For example, the sample mutation rate may be equal to the normalized mutation counts of sample s, i.e., the total number of mutations divided by the number of bases sequenced in the sample.

Substantially mutated genes generally refer to genes that are highly mutated (occurring more frequently) in a given cancer and are generally involved in tumorigenesis.

DETAILED DESCRIPTION

Disclosed herein are techniques for detecting significantly mutated genes/pathways in a cancer cohort by modeling a gene-specific background mutation rate, which may help to understand the underlying tumorigenesis and thus may benefit therapeutic treatment. More specifically, a driver gene detection technique taking into account the heterogeneous mutational context in a cancer cohort is disclosed. A statistical model can be used to model the gene-specific background mutation rate based on a distribution of silent mutations measured from tumor samples. The gene-specific background mutation rate may then be used to detect gene/pathway enrichment and distinguish tumor suppressors and oncogenes based on the spatial distribution of the non-silent mutations, the loss-of-function mutations, and/or the gain-of-function mutations. The background mutation rate learned from cohort data may also be applied to a single sample from the same cancer type to detect drivers.

To show operational results, the disclosed techniques are applied to data samples for four types of cancer from The Cancer Genome Atlas (TCGA), although other types of cancer can be analyzed. Genes identified by the disclosed techniques show higher enrichment in known cancer driver genes compared to other methods. Besides cell cycle related pathways, which highly mutate across samples, metabolic pathways are disrupted in a subset of breast cancer samples. The results from the disclosed techniques recapitulate the observation that glioblastoma mutations cluster in the Epidermal Growth Factor (EGF) binding domain of Epidermal Growth Factor Receptor (EGFR), whereas lung mutations cluster in the tyrosine kinase domain, which indicates entirely different response to EGFR-targeted drugs. As another example, the disclosed techniques are also applied to 1059 lung adenocarcinoma (LUAD) and lung squamous cell carcinoma (LUSC) samples. Novel driver genes are discovered using the disclosed techniques, with only a small fraction of driver genes shared by the two cancer types. Most of the driver genes discovered in lung adenocarcinoma samples are tumor suppressors, whereas there is a predominance of oncogenes in the driver genes discovered in lung squamous cell carcinoma samples.

I. DETECTING DRIVER GENES AND PATHWAYS FOR DIAGNOSIS AND TREATMENT

Cancer sample accumulates mutations during cell division. The majority of the mutations arise due to the intrinsic biological processes (i.e., background mutation), such as cell division. A small portion of the mutations (called driver mutations) may occur more frequently in a given cancer and are involved in tumorigenesis. Silent mutations (mutations that do not cause amino acid changes) occur according to the background mutation rate, and candidate driver gene typically have more non-silent mutations than expected (different from the background mutation rate). Identifying the driver genes or mutations for a type of disease can help to understand the underlying tumorigenesis of the disease and thus may benefit medical diagnosis and therapeutic treatment.

FIG. 1 is a flow chart 100 illustrating an example method of detecting driver genes and pathways for diagnosis and treatment, according to certain aspects of this disclosure. In the example method, sequence data for samples having a same type of disease may be used to determine an expected number of (non-silent) mutations for a gene in the samples and an actual number of non-silent mutations for the gene in the samples, the expect number and the actual number may be compared to detect driver genes. Similar methods may be used to detect Tumor Suppressor Genes (TSGs), Oncogenes (OGs), and Significantly Mutated Pathways (SMP). The detected driver genes, mutations, and/or pathways may then be used for diagnosis and treatment of the disease.

At block 110, samples having a same type of disease may be received and sequenced and the mutations may be identified based on the sequence data. Techniques for sequencing DNA samples and measuring the mutations in the samples are described in detail in Section II of this disclosure.

At block 120, actual numbers of mutations (more specifically, non-silent mutations) in one or more genes in the samples may be counted based on the sequencing data as described in Sections II and V of this disclosure.

At block 130, expected numbers of non-silent mutations in the one or more genes in the samples may be estimated from statistical analysis of the sequencing data. Detailed techniques for determining the expected numbers of non-silent mutations in the one or more genes in the samples are described in Sections III-VI of this disclosure. Advantages of the techniques for determining the expected numbers of non-silent mutations disclosed herein are described in Section VII of this disclosure.

At block 140, the expected number non-silent mutations in the one or more genes in the samples and the actual number non-silent mutations in the one or more genes in the samples may be compared to detect cancer driver genes, mutations, and/or pathways. For example, genes that have excessive numbers of non-silent mutations than the estimated numbers of non-silent mutations across samples may be identified as candidate driver genes. Detailed techniques for detecting cancer driver genes, mutations, and/or pathways are described in Sections V and VI of this disclosure. Example analysis results using the techniques disclosed herein are described in Section VIII of this disclosure.

At block 150, diagnosis assay and/or treatment for the type of disease may be determined based on the identified driver genes and/or pathways. Detailed techniques for determining diagnosis assay and/or treatment are described in Section IX of this disclosure.

II. SEQUENCING SAMPLES

The sequences of biological samples can be obtained from any source (public or private) in a suitable manner. The sequences can be obtained using any suitable sequencing technique. The analysis of the sequences may be performed using an analysis system. An example sequence analytical system is described below.

Figure 2:
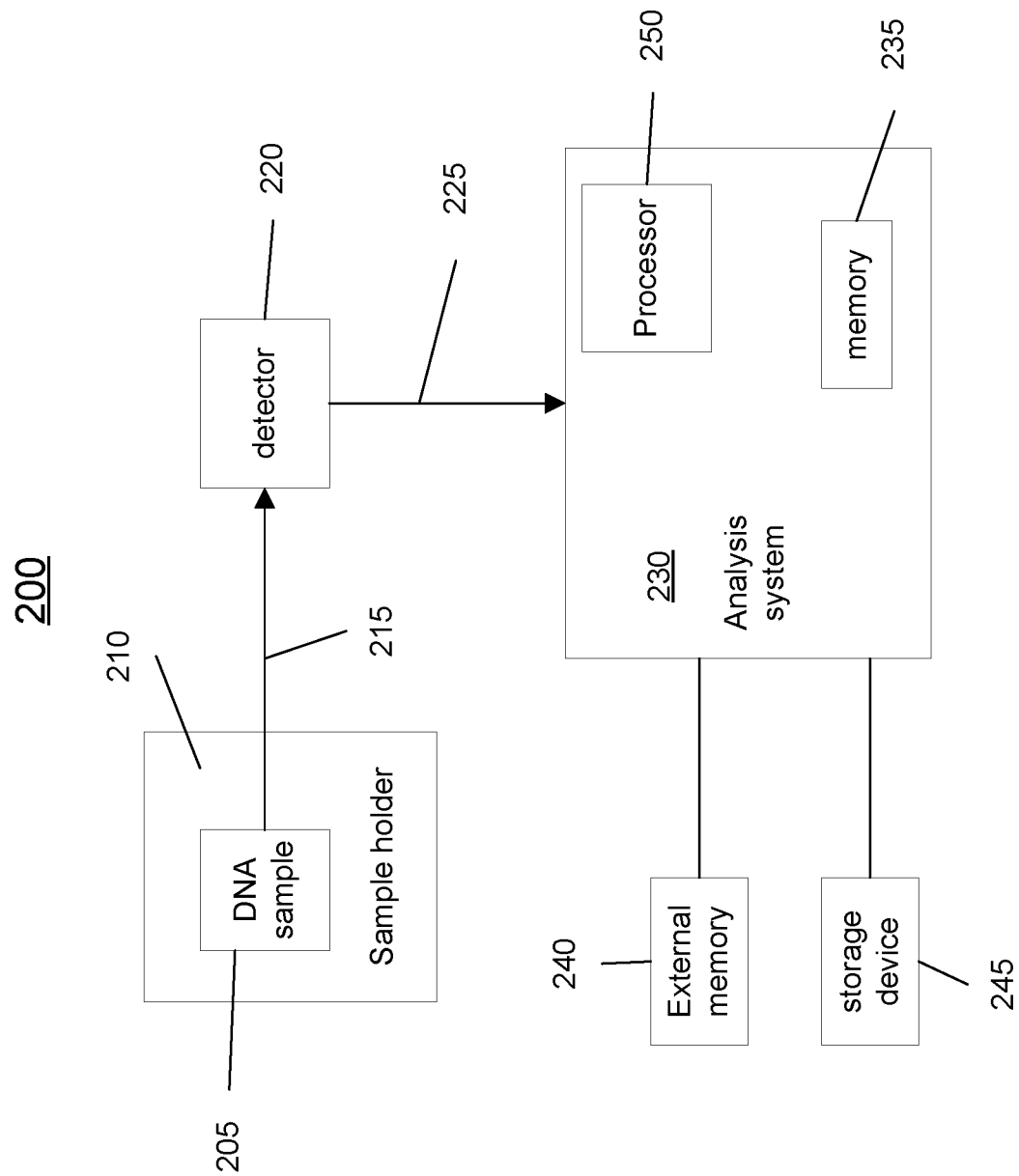
FIG. 2 illustrates an example sequence analytical system, according to an aspect of this disclosure.

FIG. 2 illustrates a sequence analytical system 200 according to an embodiment of the present invention. System 200 as shown includes a sample 205, such as a DNA molecule, within a sample holder 210, e.g., a flow cell or a tube containing droplets of DNA. A physical characteristic 215, such as a fluorescence intensity value, from sample 205 is detected by a detector 220. A data signal 225 from detector 220 can be sent to analysis system 230, which may include a processor 250 and a memory 235. Data signal 225 may be stored locally in analysis system 230 in memory 235, or externally in an external memory 240 or a storage device 245.

Detector 220 can detect a variety of physical signals, such as light (e.g., fluorescent light from different probes for different bases) or electrical signals (e.g., as created from a molecule traveling through a nanopore).

Analysis system 230 may be, or may include, a computer system, ASIC, microprocessor, etc. It may also include or be coupled with a display (e.g., monitor, LED display, etc.) and a user input device (e.g., mouse, keyboard, buttons, etc.). Analysis system 230 and the other components may be part of a stand-alone or network connected computer system, or they may be directly attached to or incorporated in a thermal cycler device. Analysis system 230 may also include optimization software that executes in processor 250.

Based on the sequencing data, mutations in one or more genes in the samples may be counted. Mutations may generally be classified as silent or non-silent based on whether they cause a change to the amino acid sequence of the translated protein. It is assumed that whether a background mutation causes a silent or non-silent effect depends solely on the nucleotide change, and silent mutations occur according to a background mutation rate. From sequencing data collected from the samples, the numbers of silent mutations and non-silent mutations in each gene in each sample can be counted.

To estimate the background mutation rate of tumor samples, possible tri-nucleotide contexts (including 6 possible type of single base substitutions—C/G>A/T, C/G>G/C, C/G>T/A, T/A>A/T, T/A>C/G, T/A>G/C—and possible nucleotide contexts around each single base substitution) and indel mutation contexts may be considered. For example, a total of 97 mutation contexts (96 tri-nucleotide contexts and an indel mutation context) may be considered. Since the substitution of A to C is the same as T to G, the number of possible types of substitutions is 6. Then, 4 options for each neighbor positions, provides 6×4×4=96 possible tri-nucleotide contexts.

For each tri-nucleotide mutation context i of the, for example, 96 mutation contexts, the number of silent $n_{i(silent)}$ and non-silent $n_{i(nonsilent)}$ mutations observed across all tumor samples and the number of possible silent $N_{i(silent)}$ and non-silent $N_{i(nonsilent)}$ variants in an exome may be determined. For non-silent mutations, only genes that are less likely to be drivers, e.g., genes mutated in fewer samples, are taken into consideration to avoid skewing the non-silent mutation rate. For example, in some embodiments, the bottom fraction, e.g., 60%, of genes ranked based on the number of samples having at least one non-silent mutation in that gene may be used. The potential bias introduced by using a subset of genes with non-silent mutations can be corrected by a factor r, which may be estimated using the method of moment:

$$r = \frac{1}{96}\sum_{i=1}^{96} \frac{\frac{n_i(\text{nonsilent})}{N_i(\text{nonsilent})}}{\frac{n_i(\text{silent})}{N_i(\text{silent})}}. \qquad (1)$$

For mutation context i, the context mutation rate $m_i$ maybe calculated as:

$$m_i = \frac{n_i(\text{silent}) + n_i(\text{nonsilent})}{N_i(\text{silent}) + r \times N_i(\text{nonsilent})}. \qquad (2)$$

The indel mutation rate $m_{indel}$ may be calculated as:

$$m_{indel} = \frac{n(\text{indel})}{L}, \qquad (3)$$

where L is the whole exome length. It may be assumed that all protein-coding positions can have indels, and that all indels are non-silent. In-frame and frame-shift indels are not differentiated at this point.

Because samples from different individuals are expected to have different background mutation rates, a sample specific factor (i.e., sample mutation rate) $b_s$ may be used to represent the total mutation burden of a sample s. More specifically, $b_s$ may be equal to the normalized mutation counts of sample s, i.e., the total number of mutations divided by the number of bases sequenced in the sample.

For a gene g, context-specific mutation rates for all possible bases that could mutate to silent mutations can be added to determine the expected silent mutation rate $E_{g(silent)} = \Sigma_{silent\ base}\ m_i$. The expected number of silent mutations for a given gene and sample may be determined based on the sample mutation rate ($b_s$), the expected silent mutation rate $E_{g(silent)}$, and a gene-specific value (coefficient).

The expected number of non-silent mutations for a given gene and sample may be determined in a manner similar to the number of silent mutations described above. Specifically, for each base that could mutate to a non-silent mutation in gene g, the mutation rate $m_i$ for context i may be determined. Context-specific mutation rates for all possible bases in gene g that could mutate to non-silent mutations can be added to determine the expected non-silent mutation rate $E_{g(nonsilent)}$. The expected number of silent mutations for a given gene and sample may be determined based on the sample mutation rate ($b_s$), the expected non-silent mutation rate $E_{g(nonsilent)}$, and the gene-specific value (coefficient).

III. DETECTION OF CANCER DRIVER GENES AND PATHWAYS

As discussed above, candidate driver genes typically have more non-silent mutations than expected (different from the background mutation rate). Thus, driver genes may be identified by comparing the expected number of non-silent mutations and the measured number of non-silent mutations in a gene.

Figure 3:
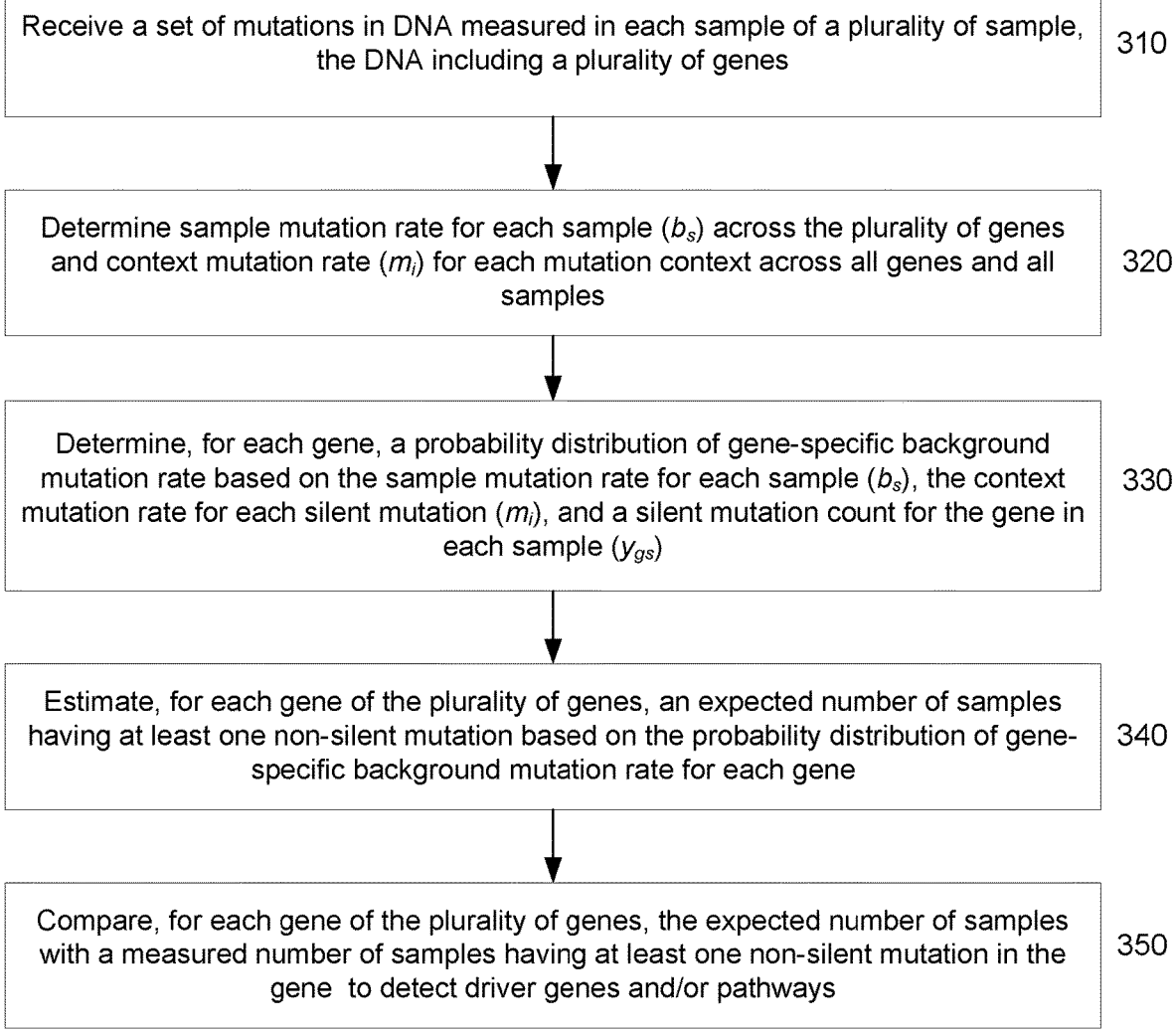
FIG. 3 is a flow chart illustrating an example method of detecting driver genes and pathways, according to certain aspects of this disclosure.

FIG. 3 is a flow chart 300 illustrating an example method of driver gene detection, according to certain aspects of this disclosure. In the example method, the sample mutation rate for each sample and the context mutation rate for each mutation context may be determined based on measured mutations in DNA in a plurality of samples from different subjects having a same type of cancer. A probability distribution of gene-specific background mutation rate (e.g., a gene-specific mean (or mean coefficient) and/or a gene-specific dispersion) for each gene may then be estimated based on measured mutations in DNA in the plurality of samples from different subjects having the same type of cancer. Based on the estimated gene-specific mean (or mean coefficient) and/or gene-specific dispersion, the sample mutation rate for each sample, and the context mutation rate for each mutation context, an expected number of samples having at least one non-silent mutation may be determined for each gene and compared with actual number of non-silent mutations in each gene determined based on the measured mutations in DNA to detect cancer driver genes. Similar methods may be used to detect Tumor Suppressor Genes (TSGs), Oncogenes (OGs), and Significantly Mutated Pathways (SMP).

At block 310, for each sample of a plurality of samples from different subjects having a same type of cancer (e.g., breast cancer, lung cancer, colon cancer, etc.), a set of mutations in DNA may be measured for a plurality of genes in each sample. The measured mutations in DNA may be provided to an analytical system for estimating the gene-specific background mutation rate and detecting cancer driver genes, mutations, and/or pathways. Techniques for measuring the mutations in DNA are described above in Section II of this disclosure.

At block 320, a sample mutation rate for each sample across the plurality of genes and a context mutation rate for each mutation context across the plurality of genes and the plurality of samples may be calculated based on the sets of mutations in DNA measured for the plurality of genes in the plurality of samples. The sample mutation rate may be determined based on the total number of mutations in a sample (sample mutations). The mutation context rate may be determined based on the number of mutations in each context of flanking trinucleotide (mutation context), where each mutation context may correspond to a type of substitution or deletion. Detailed techniques for determining the sample mutation rate and the context mutation rate are described above in Section II of this disclosure.

At block 330, a probability distribution of gene-specific background mutation rate for each gene including a gene-specific mean (or a gene-specific mean coefficient) and/or a gene-specific dispersion may be determined based on the sample mutation rate for each sample, the context mutation rate for each silent mutation, and a silent mutation count for each gene in each sample calculated from the set of mutations in DNA measured for the plurality of genes in each sample. For example, the probability distribution of gene-specific background mutation rate for each gene may also be determined by considering each gene independently and by fitting gene-specific background mutation rates for all samples for each gene to a model for probability distribution (e.g., negative binomial distribution, Poisson distribution, beta binomial distribution, etc.) for the gene. This technique may consider unknown influencing factors, but may be vulnerable to noise.

In some embodiments, the gene-specific mean coefficient for each gene may be determined by considering known mutation influencing factors using a regression technique (e.g., negative binomial repression, Poisson regression, linear regression, etc.) applied to all genes and all samples. This technique may provide the shared effects of the influencing factors on background mutation rate, but may not be accurate as the effects of many unknown factors are not considered.

In some embodiments in this disclosure, the probability distribution of the gene-specific background mutation rate estimated using the above two techniques may be used as prior knowledge to recursively optimize the model for probability distribution of gene-specific background mutation rate for each gene that best fits the measurement data, using, for example, Bayesian inference or non-Bayesian inferences (e.g., classical Frequentist Prediction, likelihood-based inference, etc.). Detailed techniques for determining the probability distribution of gene-specific background mutation rate for each gene are described in Section IV of this disclosure.

At block 340, the expected number of samples having at least one non-silent mutation may be estimated for each gene, based on the probability distribution of background mutation rate for the gene, the sample mutation rate for each sample, and the context mutation rate for each non-silent mutation. Detailed techniques for determining the expected number of non-silent mutations for each gene in each sample are described in Section V of this disclosure.

At block 350, for each gene of the plurality of genes, the expected number of samples having at least one non-silent mutation in the gene may be compared with the measured number of samples having at least one non-silent mutation in the gene determined based on the sets of mutations in DNA to detect cancer driver genes, mutations, and/or pathways. For example, genes that have excessive number of non-silent mutations than the estimated background mutations across samples may be identified as candidate driver genes. In some embodiments, genes that have excessive loss-of-function mutations may be identified as Tumor Suppressor Genes (TSGs), and genes that demonstrate mutational hotspots may be identified as Oncogenes (OGs). In some embodiments, pathways that are significantly mutated in a particular sample or across multiple samples may be identified as Significantly Mutated Pathways (SMP). Detailed techniques for detecting cancer driver genes, mutations, and/or pathways are described in Section V of this disclosure.

IV. ESTIMATION OF THE BACKGROUND SOMATIC MUTATION RATE

Proper modeling of the background mutation profile (affected by many known and unknown factors, such as trinucleotide context, gene length, expression level and replication timing) is critical to improving precision and recall in driver detection. Techniques for estimating background somatic mutation rates as described above in block 130 of FIG. 1 and block 330 of FIG. 3 are described in detail in this section. Section IV (A) describes example methods of estimating background mutation rate. Section IV (B) describes an example method of estimating background mutation rate using a negative binomial model. Section IV (C) describes an example method of estimating background mutation rate using a Poisson model.

A. Example Methods of Modeling Background Mutation Rate

Techniques with and without explicit consideration of known gene mutation influencing factors may be used to determine a statistical model for the gene-specific background mutation rate for each gene. In some embodiments, inference techniques may be used to optimize the statistical model for the gene-specific background mutation rate. In some embodiments, the statistical model for the gene-specific background mutation rate for each gene may be a negative binomial distribution, a Poisson distribution, or a beta binomial distribution, and a gene-specific mean (including a gene-specific mean coefficient) and/or a gene-specific dispersion for the statistical model may be estimated and optimized.

Figure 4:
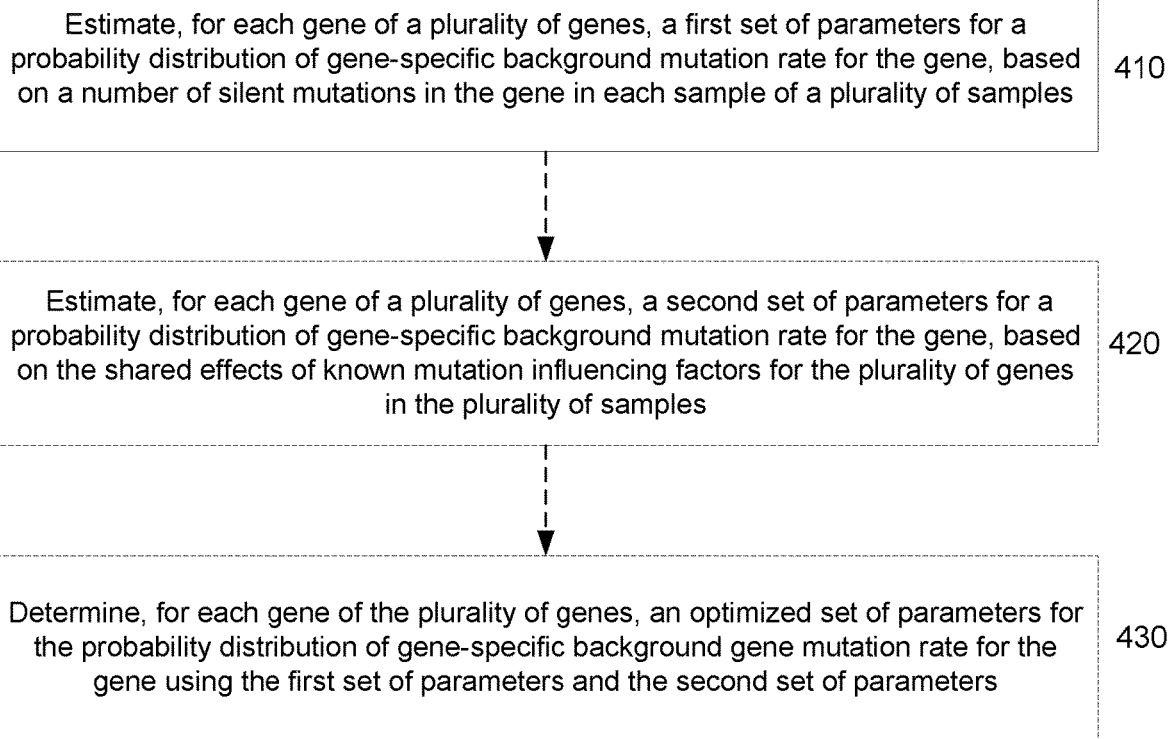
FIG. 4 is a flow chart illustrating an example method of estimating background mutation rate, according to certain aspects of this disclosure.

FIG. 4 is a flow chart illustrating an example method 400 of estimating background mutation rate described above in block 130 of FIG. 1 and block 330 of FIG. 3, according to certain aspects of this disclosure.

At block 410, a first set of parameters for the probability distribution of gene-specific background mutation rate for each gene may be determined by considering the plurality of samples for the gene. The first set of parameters may include a first gene-specific mean (or gene-specific mean coefficient) and/or a gene-specific dispersion for the probability distribution. The first set of parameters may be determined by fitting the probability distribution to measured background gene mutation rates for the plurality of samples for the gene based on a number of silent mutations in the gene in each sample of the plurality of samples. The probability distribution for each gene may include a negative binomial distribution, a Poisson distribution, or a beta binomial distribution. This technique may consider unknown influencing factors, but may be vulnerable to noise. Some embodiments of determining the first set of parameters are described in Section IV (B)(2) and Section IV (C) of this disclosure.

Optionally, at block 420, a second set of parameters for a probability distribution of gene-specific background mutation rate for each gene of a plurality of genes, such as a second gene-specific mean (or gene-specific mean coefficient) and/or a dispersion for the probability distribution, may be determined by considering known influencing factors, such as replication timing (R), expression level (X), open-chromatin state (C), and whether gene is an olfactory receptor (O). The dispersion, if used, may be non-gene-specific and may be a genome-wide dispersion. The second set of parameters may be determined using a regression technique (e.g., negative binomial repression, Poisson regression, linear regression, etc.) applied to measurement results for the plurality of genes and a plurality of samples for estimating the shared effects of the known mutation influencing factors on any gene in the genome. For example, the total number of silent mutations in all samples for each gene may be used as one data point for determining the second set of parameters for the probability distribution. This technique may provide the shared effects of the mutation influencing factors on background mutation rate, but may not be accurate as the effects of many unknown factors are not considered. Some embodiments of determining the second set of parameters are described in Section IV(B)(1) and Section IV (C) of this disclosure.

Optionally, at block 430, an optimized set of parameters for the probability distribution of gene-specific background mutation rate for each gene of the plurality of samples that best fits measurement data may be determined. The first set of parameters and the second set of parameters estimated using the techniques described above at block 410 and 420 may be used as prior knowledge to recursively optimize the set of parameters for the probability distribution of gene-specific background mutation rate for the gene that best fits the measurement data, using, for example, Bayesian inference or non-Bayesian inferences (e.g., classical Frequentist Prediction, likelihood-based inference, etc.). Some embodiments of determining the optimized set of parameters are described in Section IV (B)(3) and Section IV (C) of this disclosure.

In various embodiments, depending on the statistical model used, other parameters for the probability distribution of the gene-specific background mutation rate for a gene may be determined using similar techniques. For example, when negative binominal model is used, a gene-specific dispersion may be determined by optimizing a gene-specific dispersion based on a gene-specific dispersion estimated across genes (non-gene-specific) and a gene-specific dispersion independently estimated for each gene. Other techniques, such as beta binomial distribution, may also be used to estimate the background mutation rate by optimizing a gene-specific probability distribution of the gene-specific background mutation rate based on a probability distribution of the gene-specific background mutation rate estimated using known mutation influencing factors across genes, and a probability distribution of the gene-specific background mutation rate independently estimated for each gene without explicitly considering the effects of known mutation influencing factors.

B. Estimation of the Background Mutation Rate with Negative Binomial

A statistical model, for example, a negative binomial model, for estimating the background mutation rate for a gene can be generated, based on the context mutation rate, sample mutation rate, and a number of silent mutations for each gene in each sample of a plurality of samples described above in Section II of this disclosure.

1. Estimate Background Mutation Rate Using Regression Across Genes with Consideration of Only Known Influencing Factors Assuming that the silent mutation rate may represent the background mutation rate, the number of silent mutations per gene can be modeled using the negative binomial model to take into account potential over-dispersion.

There might be multiple factors that could influence the underlying mutation rate for modeling the silent mutation counts. First, the number of possible silent mutations is controlled by the gene's coding sequence (e.g. codons and length). More specifically, for a gene g, context-specific mutation rates for all possible bases that could mutate to silent mutations can be added to determine the expected number of silent mutations $E_{g(silent)} = \Sigma_{silent\ base}\ m_i$.

Second, because samples from different individuals are expected to have different background mutation rates, a sample specific factor (i.e., sample mutation rate) $b_s$ may be used to represent the total mutation burden of a sample s. More specifically, $b_s$ may be equal to the normalized mutation counts of sample s, i.e., the total number of mutations divided by the number of bases sequenced in the sample).

Third, several additional factors may influence the underlying mutation rate for a given gene, including replication timing (R), expression level (X), open-chromatin state (C), and whether gene is an olfactory receptor (O). Values for the replication timing, expression level, and open-chromatin state may be extracted as described in M. S. Lawrence et al., "*Mutational heterogeneity in cancer and the search for new cancer-associated genes*," Nature 499, 214-8 (2013). Effect of these factors can be estimated using negative binomial regressions as described below with respect to Equations (4) and (5). R, X, and C may be numerical values and O many be a binary value (0/1). These values can be determined by averaging across different cell lines. The values can be fixed for a given determination of mutation properties for a set of samples. These values can also be updated to be cell-line specific values for use in another determination of mutation properties.

Assuming a common dispersion $\phi$ across genes, the silent mutation count $y_{gs}$ of gene g and sample s may be modeled with the following negative binomial model:

$$y_{gs} \sim NB(\text{mean}=\alpha_g b_s E_{g(silent)}, \text{dispersion}=\phi), \quad (4)$$

where $$\ln \alpha_g = \beta_0 + \beta_1 R_g + \beta_2 X_g + \beta_3 C_g + \beta_4 O_g, \quad (5)$$

$\beta = \{\beta_0, \beta_1, \beta_2, \beta_3, \beta_4\}$ is estimated by running regression using all genes and all samples.

In the regression, the values of $\beta$ and the value of $\phi$ are optimized to reduce the error of the expected number of silent mutation in each gene for each sample according the distribution (in this case the negative binomial distribution) relative to the measured number of silent mutations in the gene for that sample. The values for R, X, C, and O do vary for each gene, and thus a gene-specific value $\alpha_g$ is obtained, although the values for $\beta$ are not gene-specific. Herein, the gene-specific value $\alpha_g$ is one example of a gene-specific mean coefficient, as it multiplies $b_s E_{g(silent)}$.

The value determined for $\alpha_g$ is determined based on known factors due to the parameterization using R, X, C, and O. But, there are unknown factors that can affect the background mutation rate. The determination of the gene-specific mean value to capture unknown factors is labeled as $\widehat{\alpha_g}$. But, just determining the $\widehat{\alpha_g}$ without any constraints can lead to inaccurate results. The sections below discuss an initial determination of $\widehat{\alpha_g}$ and further optimization with a level of constraint based on the gene-specific value $\alpha_g$ determined from known factors.

2. Estimate Background Mutation Rate Using Single Gene Analysis with Consideration of Unknown Influencing Factors As described above, in Equations (4) and (5), it is assumed that a common dispersion can be used for all genes. However, in real samples, the dispersion of mutations counts varies widely across genes. As in the analysis of count data from RNA-Seq experiments, where accurately modeling the distribution of count data is essential to detecting differences in counts in a particular gene, here, read counts for a given gene can also be effectively modeled using the negative binomial model, and the dispersion parameter of the negative binomial model may be used to represent any additional variance in read counts that is not captured by a Poisson distribution of read counts. A gene-specific dispersion may be applied to capture unknown factors affecting variance in read counts for a gene as described in, for example, M. D. Robinson & G. K Smyth, "*Moderated statistical tests for assessing differences in tag abundance,*" Bioinformatics 23, 2881-7 (2007).

For each gene, the Maximum Likelihood Estimation (MLE) can be used to estimate gene-specific dispersion $\phi_g$ and $\widehat{\alpha_g}$ by maximizing:

$$P(Y_g | \widehat{\alpha_g}, \phi_g) = \prod_s \frac{\Gamma(y_{gs} + \phi_g^{-1})}{\Gamma(\phi_g^{-1})\Gamma(y_{gs}+1)} \left( \frac{1}{1+\widehat{\alpha_g} b_s E_{g(silent)} \phi_g} \right)^{\phi_g^{-1}} \left( \frac{\widehat{\alpha_g} b_s E_{g(silent)}}{\phi_g^{-1} + \widehat{\alpha_g} b_s E_{g(silent)}} \right)^{y_{gs}} \quad (6)$$

for each gene, rather than pooling genes, where $Y_g = \{y_{g1}, y_{g2}, \ldots, y_{gs}\}$ are the silent mutation counts in different samples, the initial value of $\widehat{\alpha_g}$ is given by $$\widehat{\alpha_g} = \frac{1}{s} \sum_1^s \frac{y_{gs}}{b_s E_{g(silent)}},$$

and the influencing factors (R, X, C, O) are not considered.

The function in Equation (6) is probability mass function corresponding to the binomial distribution. The value of P is optimized for a given gene g by varying $\widehat{\alpha_g}$ and $\phi_g$. This process can be viewed as a similar process as Equation (4), where a is not constrained by a specific parameterization, as in Equation (5). This allows $\widehat{\alpha_g}$ to encompass unknown factors in estimating the background mutation rate.

3. Optimize Gene-Specific Mutation Rate and/or Dispersion by Combining the Above Two Techniques Because $\alpha_g$ may be obtained by pooling all genes together, it may capture the common trend of the influencing factors (R, X, C, O) on background mutation rate. On the other hand, $\widehat{\alpha_g}$ is a gene-specific parameter independent of the influencing factors. $\widehat{\alpha_g}$ and $\alpha_g$ are not always the same, which could be caused by technical noises (e.g. errors in mutation calling algorithms) or reflect real biological mechanisms (e.g. factors influencing the background mutation rate that are not included in our regression model). Due to the low number of somatic mutations in each gene, $\widehat{\alpha_g}$ may be vulnerable to technical noises. An optimized $\alpha'_g$ may be determined by incorporating $\alpha_g$ from NB regression model and those determined from gene-specific estimation, namely $\widehat{\alpha_g}$ and $\phi_g$. The posterior probability of $\alpha'_g$ may be proportional to the likelihood times prior:

$$P(\alpha'_g | Y_g, \alpha_g, \phi_g, \widehat{\alpha_g}) \propto P(\alpha'_g | \alpha_g, \widehat{\alpha_g}) \prod_s P(y_{gs} | \alpha'_g, \phi_g), \quad (7)$$

$$y_{gs} \sim NB(\alpha'_g b_s E_{g(silent)}, \phi_g), \text{ and} \quad (8)$$

$$P(\alpha'_g | \alpha_g, \widehat{\alpha_g}) = \frac{1}{\sigma \sqrt{2\pi}} e^{-\frac{(\ln \alpha'_g - \ln \alpha_g)^2}{2\sigma^2}}, \quad (9)$$

where $\sigma$ may be estimated by:

$$\sigma = \sqrt{\frac{1}{N} \sum_g (\ln \alpha_g - \ln \widehat{\alpha_g})^2}. \quad (10)$$

The optimized $\alpha'_g$ for each gene may be the $\alpha'_g$ that can maximize Equation (7).

The prior probability distribution in Equation (7) is chosen to constrain $\alpha'_g$ to be centered at $\alpha_g$. $P(y_{gs}|\alpha'_g, \phi_g)$ corresponds to Equation (6).

The steps of gene-specific dispersion estimation and optimization of gene mean may be repeated by replacing $\widehat{\alpha_g}$ with $\alpha'_g$ and re-estimate dispersions until a convergence is achieved. For example, the $\alpha_g$ can be used in Equation (6), and a new $\phi_g$ may be determined while keeping $\alpha'_g$ fixed. The new $\phi_g$ can then be used in Equation (7) to determine a new $\alpha'_g$ (with the constraint of the chosen prior probability distribution). The process can continue until convergence is obtained. The estimated $\alpha'_g$ and $\phi_g$ can then be used in the following steps described in, for example, Section IV.

C. Estimation of the Background Mutation Rate with Poisson Regression

In some embodiments, an alternative (and less computationally intensive) technique using Poisson regression may be used. More specifically, the background mutation may be modeled using a Poisson distribution as described by Equations (11) and (12) below, similar to Equations (4) and (5) described above for negative binomial regression.

$$y_{gs} \sim \text{Poisson}(\alpha_g b_s E_{g(silent)}), \tag{11}$$

where $$\ln \alpha_g = \beta_0 + \beta_1 R_g + \beta_2 X_g + \beta_3 C_g + \beta_4 O_g. \tag{12}$$

For each gene, the $\widehat{\alpha_g}$ can be determined by:

$$\widehat{\alpha_g} = \frac{\sum_s y_{gs}}{\sum_s b_s E_{g(silent)}}. \tag{13}$$

The optimized $\alpha'_g$ can be determined using $\alpha_g$ and $\widehat{\alpha_g}$ under Poisson regression model:

$$P(\alpha'_g \mid Y_g, \alpha_g, \widehat{\alpha_g}) \propto P(\alpha'_g \mid \alpha_g, \widehat{\alpha_g}) \prod_s P(y_{gs} \mid \alpha'_g), \tag{14}$$

$$y_{gs} \sim \text{Poisson}(\alpha'_g b_s E_{g(silent)}), \text{ and} \tag{15}$$

$$P(\alpha'_g \mid \alpha_g, \widehat{\alpha_g}) = \frac{1}{\sigma\sqrt{2\pi}} e^{\frac{-(\ln \alpha'_g - \ln \alpha_g)^2}{2\sigma^2}}, \tag{16}$$

where $\sigma$ may be estimated by:

$$\sigma \sqrt{\frac{1}{N} \sum_g (\ln \alpha_g - \ln \widehat{\alpha_g})^2}. \tag{17}$$

The optimized $a'_g$ for each gene may be the $\alpha'_g$ that can maximize Equation (14). This technique assumes a more homogenous background across samples, which may or may not be accurate depending on the cancer type under investigation.

As described above, in various embodiment, other regressions (e.g., linear regression), distributions (e.g., beta-binominal distribution), and optimization/inference techniques (e.g., non-Bayesian inference) can also be used.

V. ESTIMATION OF MUTATION RATES FOR NON-SILENT MUTATIONS

In the following section, techniques for determining mutation rates of non-silent mutations for significantly mutated genes, potential tumor suppressor genes, potential oncogenes, and significantly mutated pathways are described.

A. Significantly Mutated Genes (SMG)

The number of possible non-silent mutations for a given gene and sample may be determined in a manner similar to the number of silent mutations described above. Specifically, for each base that could mutate to a non-silent mutation in gene g, the mutation rate $m_i$ for context i may be determined. In addition, an estimate of indel rate in the gene may be included by calculating the length $l_g$ of the gene g times the indel mutation rate $m_{indel}$. The expected mutation rate of non-silent mutations for a gene is then given by:

$$E_{g(silent)} = l_g * m_{indel} + \sum_{nonsilent\ base} m_i. \tag{18}$$

For a given sample s and given gene g, the expected number of non-silent mutations $v_{gs}$ under the background mutation rate may be calculated by:

$$v_{gs} = \alpha'_g b_s E_{g(nonsilent)}. \tag{19}$$

The probability of observing at least one non-silent mutation of gene g in sample s is $$1 - P(Y=0), \text{ where}.$$

$$P(Y=0) = \frac{1}{\Gamma(1)} \left( \frac{1}{1 + v_{gs}\phi_g} \right)^{\phi_g^{-1}}, \tag{20}$$

$\phi_g$ is the gene specific dispersion, and $v_{gs}$ is given by Equation (19).

Significantly mutated genes may be considered as those highly mutated across samples, instead of having high number of non-silent mutations within a particular sample. The number of samples with non-silent mutations in gene g may be counted and a Poisson binomial model may be applied to test whether gene g is highly mutated across samples.

For example, the value from (20) can be used to determine the expected number of samples that have at least one non-silent mutation for the gene. A difference between the actual number and the expected number can be ranked or used to determine a p-value that can be ranked. The top genes can be identified, e.g., where the top is a specific number or a percentage.

B. Potential Tumor Suppressor Genes (TSGs)

A similar determination may be made for a subset of non-silent mutations, e.g., for nonsense mutations. Tumor suppressor genes may contribute to tumorigenesis through inactivation. TSGs may be enriched for loss-of-function (LOF) mutations throughout their gene length. Instead of considering all non-silent mutations, whether a gene is highly disrupted by loss-of-function mutations (nonsense and frame-shift indels) may be determined. Similar techniques as discussed above with respect to SMG may be used for detecting TSGs, such that:

$$E_{g(LOF)} = l_g * f * m_{indel} + \sum_{nonsense\ base} m_i, \tag{21}$$

Where $$f = \frac{n(\text{frameshift indels})}{n(\text{indels})}. \tag{22}$$

A frame-shift indel (insertion or deletions) is of a number of nucleotides in a DNA sequence that is not divisible by three. Due to the triplet nature of gene expression by codons, the insertion or deletion can change the reading frame (the grouping of the codons), resulting in a completely different translation from the original.

C. Potential Oncogenes (OGs)

Unlike tumor suppressors, oncogenes cause tumorigenesis by gain-of-function mechanisms. Activating mutations may recurrently occur at the same amino acid positions. For oncogenic activity, whether missense mutations are clustered in particular amino acids of the protein may be determined. Samples may be pooled together for the determination.

To correct for the mutations occurred due to the background mutation rate, a gene-specific correction factor cg may be used:

$$c_g = \max\left(0, 1 - \frac{\text{expected (missense mutations)}}{\text{observed (missense mutations)}}\right). \quad (23)$$

The expected number of missense mutation may be given by $\alpha_g E_{g(missense)} \Sigma_s b_s$ (pooling samples).

The amino acid positions may be obtained for all somatic mutations. In case of multiple proteins from a same gene, the protein with the most somatic mutations is chosen. For the chosen protein, the binomial test may be perform for each amino acid a:

$$\text{binom}(n^*c_g, N^*c_g, p=p_a(\text{missense})), \quad (24)$$

where n is the number of mutations observed in a, N denotes the total number of mutations observed for the protein, and $$p_a(\text{missense}) = \frac{E_{a(missense)}}{\sum_{\text{all } b \text{ of the protein}} E_{a(missense)}}$$

denotes the probability of observing a missense mutation at the given amino acid, in which $E_{a(missense)} = \Sigma_{missense\ in\ a} m_i$. Thus, the gene-specific $\alpha'_g$ can be used to identify amino acids that have a higher probability than expected under the background mutation rate.

Significant positions (after multiple hypothesis correction with false discovery rate (FDR)<0.05) may be grouped into clusters where their minimum distances to any other positions are less than or equal to 3 within their corresponding clusters. The binomial test may then re-applied to the identified clusters.

D. Significantly Mutated Pathways

Kyoto Encyclopedia of Genes and Genomes (KEGG) pathways may be downloaded as described in K. A. Hoadley et al., "*Multiplatform Analysis of 12 Cancer Types Reveals Molecular Classification within and across Tissues of Origin,*" Cell 158, 929-944 (2014). Pathway analysis may be similar to the SMG analysis described above. Pathways that are either significantly mutated in a particular sample or across multiple samples may be tested. For a particular sample, Poisson binomial model can be applied to test if the number of mutated genes in the pathway is significantly higher than the sample background. For cross-sample analysis, after calculating the probability of observing zero non-silent mutation of genes in sample s using Equation (20), the probability that at least one gene in the pathway is mutated can be determined by:

$$P(\geq 1 \text{ genes mutated in the pathway}) = 1 - \prod_{g \text{ in pathway}} P_g(Y=0). \quad (25)$$

The significance test can then be applied across all samples.

P-values from SMG, TSG, and OG analyses can be adjusted with multiple-hypotheses correction. Combined p-values using Fisher's method, GSMuta-Combined (FDR<0.05), may also be used. However, due to the non-independent nature of the three hypotheses, Fisher's combined p-values may not be accurate. As such, p-value ranking from the SMG, TSG, and OG analyses, rather than the combined p-values, may be used.

VI. EXAMPLE METHOD

FIG. 5 is a flow chart 500 illustrating an example method of detecting cancer driver genes, according to certain aspects of this disclosure.

At block 510, for each sample of a plurality of samples from different subjects having a same type of cancer, a set of mutations in DNA measured in the sample for a plurality of genes may be received. The plurality of samples may be measured using a system such as sequence analytical system 100 of FIG. 1. The set of mutations in DNA measured in each sample of the plurality of samples may also be obtained from a database as described in Section VIII (A).

At block 520, for each sample of the plurality of samples, a sample mutation rate ($b_s$) may be determined based on a total number of mutations measured in the sample. More specifically, the sample mutation rate ($b_s$) may be equal to the normalized mutation counts of a sample s, i.e., the total number of mutations in sample s divided by the number of bases sequenced in sample s.

At block 530, for each of a plurality of mutation contexts, a context mutation rate, such as $m_i$ and $m_{indel}$ in Equations (2) and (3), may be determined based on a first number of mutations identified in the sets of mutations for the mutation context as described above in Section IV (A). A mutation context corresponds to a type of substitution or deletion, such as a tri-nucleotide context or an indel mutation context.

At block 540, for each gene of a plurality of genes, an expected silent mutation rate ($E_{g(silent)}$) may be determine using a sum of context mutation rates of silent mutations in the gene, for example, as $E_{g(silent)} = \Sigma_{silent\ base}\ m_i$. A silent mutation is a mutation that does not cause a change to an amino acid sequence of a translated protein for the gene.

At block 550, for each gene of the plurality of genes, a probability distribution of gene-specific background mutation rate may be determined as described above in, for example, FIG. 4 and Sections IV. A first probability distribution of a gene-specific background mutation rate for the gene may be determined across the plurality of samples based on the expected silent mutation rate for the gene ($E_{g(silent)}$) and the sample mutation rate for each sample ($b_s$). The first probability distribution may be based on a statistical model, such as a negative binomial distribution, a Poisson distribution, or a beta binomial distribution. In some embodiments, determining the first probability distribution may include optimizing a gene-specific background mutation rate ($\widetilde{\alpha_g}$) (and/or a gene-specific dispersion (g) for the first probability distribution to increase a fit of the probability distribution to a second number of silent mutations in the gene measured for each sample of the plurality of sample ($y_{gs}$) using, for example, Equation (6) or (13), as described above in, for example, Section IV (B)(2) and IV (C).

Optionally, at block 550, a second probability distribution of the gene-specific background mutation rate may be determined by determining shared effects of known influencing factors on gene mutation rates for the plurality of genes and the plurality of samples. For example, a gene-specific background mutation rate ($\alpha_g$) for each gene of the plurality of genes (and/or a non-gene-specific dispersion $\phi$) may be determine using, for example, negative binomial regression, Poisson regression, or linear regression as described above in, for example, Sections IV (B)(1) and IV (C). In some embodiments, determining the gene-specific background mutation rate ($\alpha_g$) (and/or the non-gene-specific dispersion $\phi$) may include determining shared effects of known mutation influencing factors for the plurality of genes and the plurality of samples, for example, using Equations (4) and (5) for negative binomial regression or using Equations (11) and (12) for Poisson regression.

Optionally, at block 550, an optimized probability distribution of the gene-specific background mutation rate may be determined based on the first probability distribution and the second probability distribution. For example, an optimized gene-specific background mutation rate ($\alpha'_g$) (and/or gene-specific dispersion $\phi_g$) may be determined based on the gene-specific background mutation rate ($\widehat{\alpha_g}$) (and/or gene-specific dispersion $\phi_g$) for the first probability distribution, the gene-specific background mutation rate ($\alpha_g$) (and/or a non-gene-specific dispersion $\phi$) for the second probability distribution, and the number of silent mutations in the gene in each sample of the plurality of samples ($y_{gs}$), as described above in Sections IV (B)(3) and IV (C). In some embodiments, determining the optimized probability distribution of the gene-specific background mutation rate may include optimizing the gene-specific background mutation rate ($\alpha_g$) (and/or gene-specific dispersion $\phi_g$) to best fit the number of silent mutations for the gene in each of the plurality of samples. For example, the first probability distribution and the second probability distribution may be used as prior knowledge to recursively determine the optimized gene-specific background mutation rate ($\alpha'_g$) (and/or gene-specific dispersion $\phi_g$) that best fits the measurement data, using, for example, Bayesian inference (e.g., using Equations (7)-(10) or Equations (14)-(17)) or non-Bayesian inferences (e.g., classical Frequentist Prediction, likelihood-based inference, etc.).

At block 560, for each gene of the plurality of genes, a measured number of samples having at least one non-silent mutation in the sets of mutations may be counted, as described above in Section V (A).

At block 570, an expected number of samples having at least one non-silent mutation in a gene may be determined based on the optimized probability distribution of the gene-specific background mutation rate for the gene. For example, the expected number of samples having at least one non-silent mutation may be determined using P(Y=0) as described above in Section IV(A) with respect to Equations (18)-(20).

At block 580, the expected number and the measured number of samples having at least one non-silent mutation may be compared to identify a group of genes having the measured number of samples higher than the expected number of samples as candidate driver genes. For example, a likelihood value for the measured number, such as a difference of the expected number and the measured number or P(Y=0), may be obtained as described above in, for example, Sections V(A)-(D), and a group of genes having high likelihood values (e.g., above a threshold value) may be determined as candidate driver genes as described above in Section V.

The above method may be used to detect significantly mutated genes (e.g., cancer driver genes), potential tumor suppressor genes (TSGs), potential oncogenes (OGs), and/or significantly mutated pathways. It is noted that even though FIG. 5 describes the operations as a sequential process, many of the operations can be performed in parallel or concurrently. In addition, the order of the operations may be rearranged. For example, operations at blocks 520-540 may be rearranged. Operations at block 560 may be performed before operations at block 550, 540, 530, or 520. An operation may have additional steps not included in the figure. Some operations may be optional, and thus may be omitted in various embodiments. Some operations described in one block may be performed together with operations at another block. Furthermore, embodiments of the methods may be implemented in hardware, software, firmware, middleware, microcode, hardware description languages, or any combination thereof. In various embodiments, means for performing the functions in flow chart 500 may include, but are not limited to, for example, sequence analytical system 200 of FIG. 2 or computer system 10 of FIG. 17 described below.

VII. ADVANTAGES

The disclosed techniques provide several advantages over existing methods as described in detail below.

A. Estimation of the Gene-Specific Mutation Rate by Consolidating Single Gene and Cross-Genes Modeling:

Existing driver gene detection methods either do not estimate gene-specific mutation rate or only consider known influencing factors (such as gene expression, replication timing, etc.). The disclosed techniques model the mutation rate in a gene-specific manner by integrating both known and unknown influencing factors. Impact of known influencing factors can be estimated from cross-genes modeling. Single gene modeling can be used to capture per-gene variability, but may also capture technical noise. To consolidate per gene variability and reduce technical noise, the disclose techniques estimate the optimal parameters, such as gene-specific mutation rate, using maximum likelihood techniques.

B. Estimation of the Background Mutation Rate with Negative Binomial Log-Linear Mixture:

The negative binomial model has been previously used to model the occurrence of somatic mutations. However, previously used methods generally assume that the gene-specific mean calculated using the negative binomial model is accurate. The techniques disclosed herein include an optimization of the gene-specific mean that incorporates parameters $\alpha_g$ (from negative binomial) and $\widehat{\alpha_g}$, capturing both known and unknown factors that may affect gene-specific mutation rates. Further, previously used methods assume a constant dispersion across genes or other regions tested, which may not be true in real samples. The disclosed techniques use a gene-specific dispersion in somatic driver detection to account for variability across genes. In addition, while other methods may have used some gene-specific factors, such as the replication timing, expression level, open chromatin state, or whether the gene is an olfactory receptor, to model the expected mutation rate, the disclosed techniques explicitly model these gene-specific factors.

C. Significantly Mutated Genes (SMG), Potential Tumor Suppressor Genes (TSG), Potential Oncogenes (OG), and Significantly Mutated Pathways Existing methods may be available to separately identify significantly mutated genes, tumor suppressor genes, oncogenes, and significantly mutated pathways. However, the disclosed techniques couple an improved estimation of the background mutation rate with all of these additional tests, and combine multiple types of driver detection into a same method to enable direct comparisons between each type of driver gene. The background estimation is consistent for SMG, TSG, OG, and pathway analyses.

VIII. EXAMPLE RESULTS

The disclosed techniques have been applied to data samples for various types of cancer, and the results are described below.

A. Datasets

Four datasets of whole-exome somatic mutations from the TCGA data portal are analyzed using the disclosed techniques. The datasets include mutations from breast invasive carcinoma (BRCA) generated by the University of Washington, lung adenocarcinoma (LUAD) and glioblastoma multiform (GBM) by the Broad Institute, and colon adenocarcinoma (COAD) by the Baylor College of Medicine. The mutations were further filtered to include only those occurred in positions with sufficient read-depth and mapping quality (not available for COAD). Tumor samples from the same patient were combined to de-duplicate redundant mutations. In total, there were 751 BRCA samples with a median of 38 mutations, 220 LUAD samples with 198 mutations, 291 GBM samples with 72 mutations, and 217 COAD samples with 141 mutations. Mutations were re-annotated with the Variant Effect Predictor (VEP) 'pick' option to predict their unique functional effects and the mutations were transformed into Mutation Annotation Format (MAF). 1059 tumor-normal paired non-small cell lung cancer samples including 569 lung adenocarcinoma (LUAD) samples and 490 lung squamous cell carcinoma (LUSC) samples are reprocessed with SomaticSeq (as described in Fang et al., "An ensemble approach to accurately detect somatic mutations using SomaticSeq," Genome Biol., 16, 197 (2015)) to accurately call somatic mutations.

B. Whole Exome Annotation

Every protein-coding or splicing base in Ensembl GRCh37 and assigned unique functional effect can be mutated computationally. Their tri-nucleotide context (nucleotide before and after mutated base) and amino acid positions relative to the protein length are obtained.

C. Detected Genes are Enriched for Known Cancer Drivers

The enrichment of known cancer drivers from Cancer Gene Census (CGC) (genes causally implicated in cancer) is used as a benchmark to compare the performance of the method disclosed herein and the performance of other methods. The analysis results show that the genes detected using the method disclosed herein are enriched for known cancer drivers.

Figures 6A, 6B, 6C:
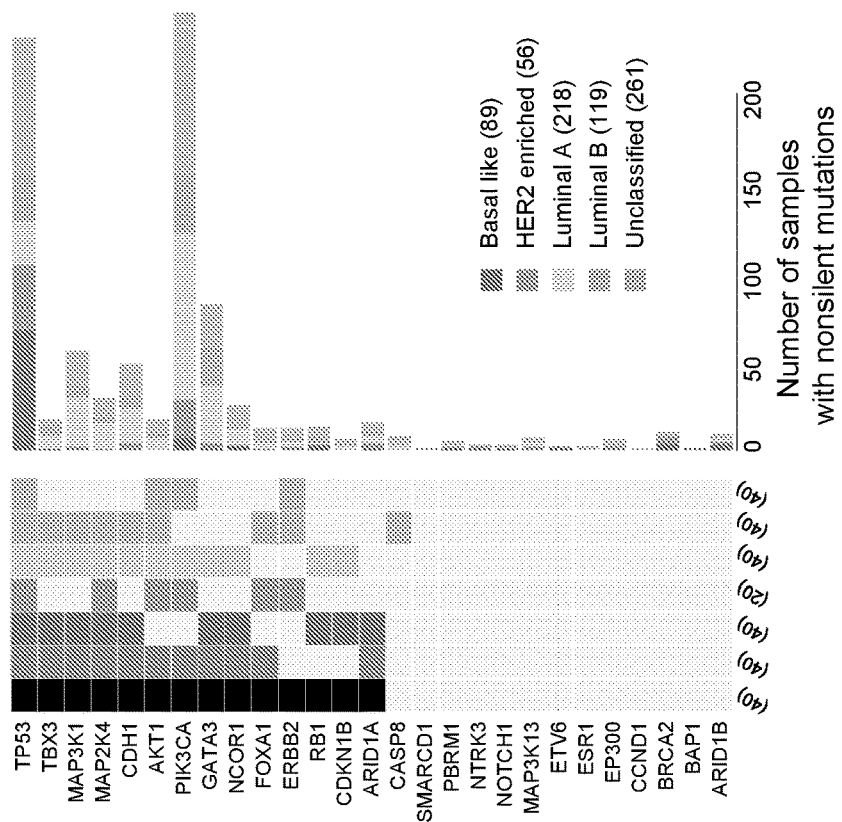
FIG. 6A illustrates the enrichment of Cancer Gene Census (CGC) (genes causally implicated in cancer), where the fraction of genes in Cancer Gene Census is calculated and plotted for genes ranked based on their p-values.
FIG. 6B illustrates breast cancer drivers detected among the top 40 known genes.
FIG. 6C illustrates detected driver genes for various breast cancer subtypes.

FIG. 6A illustrates the enrichment of Cancer Gene Census (CGC) (genes causally implicated in cancer) for BRCA, where the fraction of genes in Cancer Gene Census is calculated and plotted for genes ranked based on their p-values. Results for "GSMuta-Combined," "GSMuta-SMG," "GSMuta-TSG," and "GSMuta-OG" are analysis results using the method disclosed herein. FIG. 6A shows that the method disclosed herein performs consistently better than other methods, such as "MutSigCV Lawrence et al.," "OncodriveFM Gonzalez-Perez et al.," and "Oncodrive-Clust Tamborero et al." Furthermore, other methods, such as "MutSigCV Lawrence et al.," "OncodriveFM Gonzalez-Perez et al.," and "OncodriveClust Tamborero et al.," only provide significant p-values for genes and do not classify genes into tumor suppressors or oncogenes.

FIG. 6B illustrates breast cancer drivers detected among the top 40 known genes from "GSMuta-Combined," "GSMuta-SMG," "GSMuta-TSG," "MutSigCV Lawrence et al.," "OncodriveFM Gonzalez-Perez et al.," "Oncodrive-Clust Tamborero et al.," or top 20 genes in "GSMuta-OG." As shown in FIG. 6B, TSGs and OGs are mostly mutually exclusive, with a few exceptions, such as TP53 and MAP2K4. TSG detection is based on the assumption that nonsense and frameshift mutations lead to loss-of-function, ignoring potential loss-of-function-causing missense or in-frame mutations. Likewise, OG detection might not always capture the gain-of-function impact of missense mutations. SMG detection combines all types of non-silent mutations, which increases the statistical power but might miss mutation patterns captured by TSG detection and OG detection. Thus, the outputs from SMG detection, TSG detection, and OG detection may be used in combination when interpreting driver genes in cancer.

FIG. 6C illustrates detected driver genes for various breast cancer subtypes. The numbers of mutated samples are illustrated by bars colored based on the breast cancer subtypes defined by PAM50 mRNA expression. As shown in FIG. 6C, driver genes mutate differently among breast cancer subtypes. For example, most basal-like breast tumors contain TP53 mutations, whereas GATA3 is mostly mutated in Luminal A breast tumors.

D. Detection of Tumor Suppressors and Oncogenes

The enrichment of loss-of-function and potential gain-of-function mutations using the techniques described above based on the estimated background mutations are tested.

Figures 7A, 7B:
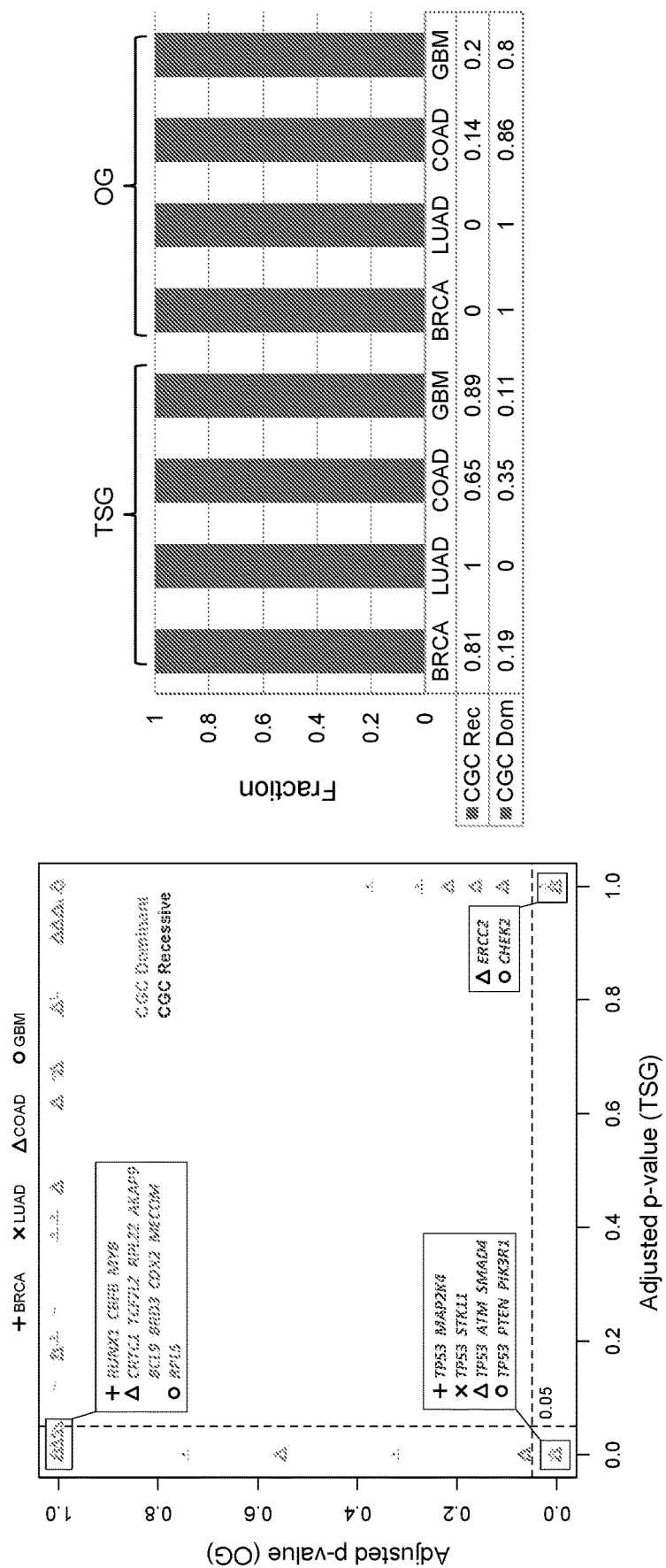
FIG. 7A illustrates the enrichment of tumor suppressor genes (TSGs) and potential oncogenes (OGs) in CGC dominant and recessive genes.
FIG. 7B illustrates the fractions of predicted TSGs and OGs in four different types of cancer.

FIG. 7A illustrates the enrichment of tumor suppressor genes (TSGs) and potential oncogenes (OGs) in CGC dominant and recessive genes. FIG. 7A shows the adjusted p-values of CGC dominant and recessive genes in four cancer types-BRCA, LUAD, COAD, and GBM. The dotted lines correspond to FDR<0.05. Generally, dominant genes are expected to be oncogenes, and recessive genes are expected to be tumor suppressor genes. However, this analysis shows that some of the genes shows inconsistency with CGC classification, suggesting possibly dual function for these genes. Dominant genes that are detected as TSG, recessive genes that are detected as OG, and genes that are detected as having both TSG and OG signals are highlighted in the boxes. For example, MYB, CBFB, and RUNX1 annotated as dominant in CGC are classified as TSGs for BRCA. In the test samples, MYB is likely deactivated in 6 BRCA samples by nonsense or frameshift mutations, 5 of which are Luminal A subtypes (the other sample is unclassified), which is supported by one study showing the potential tumor suppressor role of MYB in luminal breast cancer. Previous studies also suggested that RUNX1 could act as tumor suppressor in breast cancer. 14 test samples in the BRCA dataset are with deactivated RUNX1 and 6 of them have frameshift mutations in amino acid position 123. All these 14 samples are estrogen-receptor (ER) positive. Results in FIG. 7A suggest that driver genes may function differently in different tumor types.

FIG. 7B illustrates the fractions of predicted TSGs and OGs in the four different cancer types, annotated as CGC recessive (blue) and dominant (red), respectively. In FIG. 7B, CGC genes with significant TSG p-values (adjust p-value <0.05) are mostly recessive genes, whereas those with significant OG p-values are enriched for dominant genes. A number of genes with both TSG and OG signatures are all recessive genes as shown in FIG. 7A. Due to the uncertain impact of missense mutations (which could lead to loss-of-function or gain-of-function), those genes are considered as TSGs.

E. Mutation Hotspots on Oncogenes Vary Across Cancer Types

Figure 8:
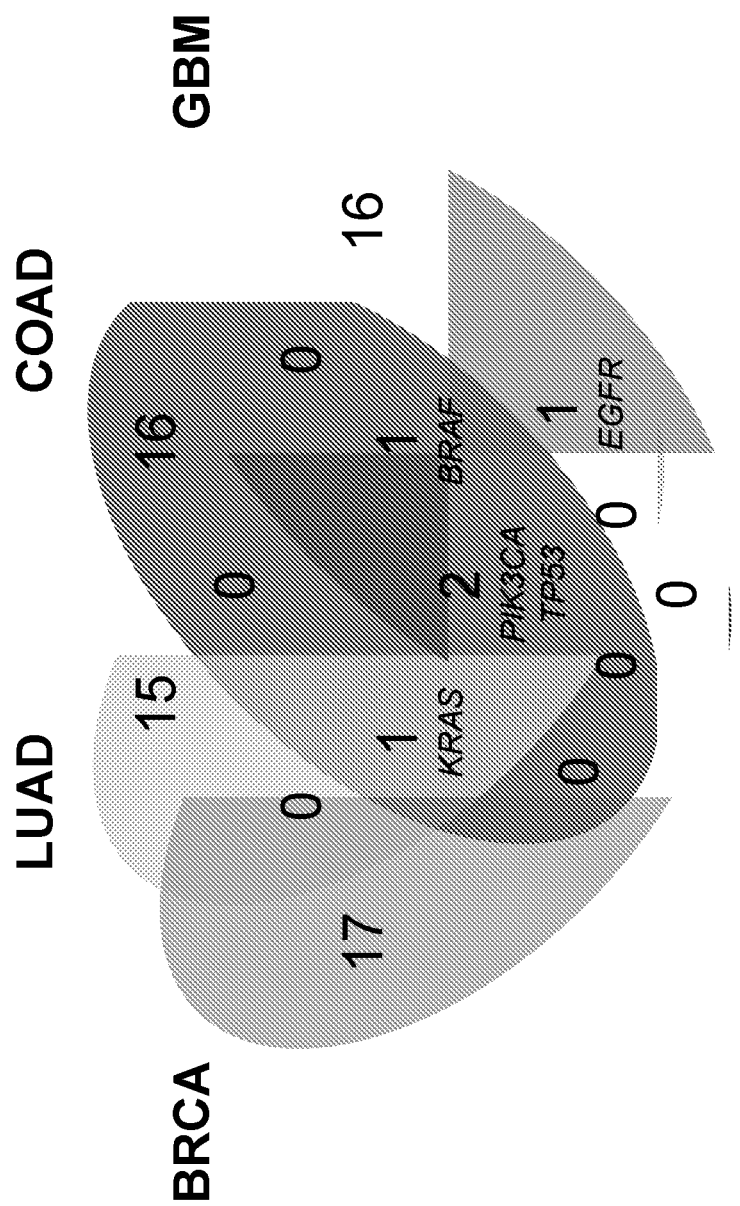
FIG. 8 illustrates the top 20 oncogenes detected in four cancer types.
Figure 9:
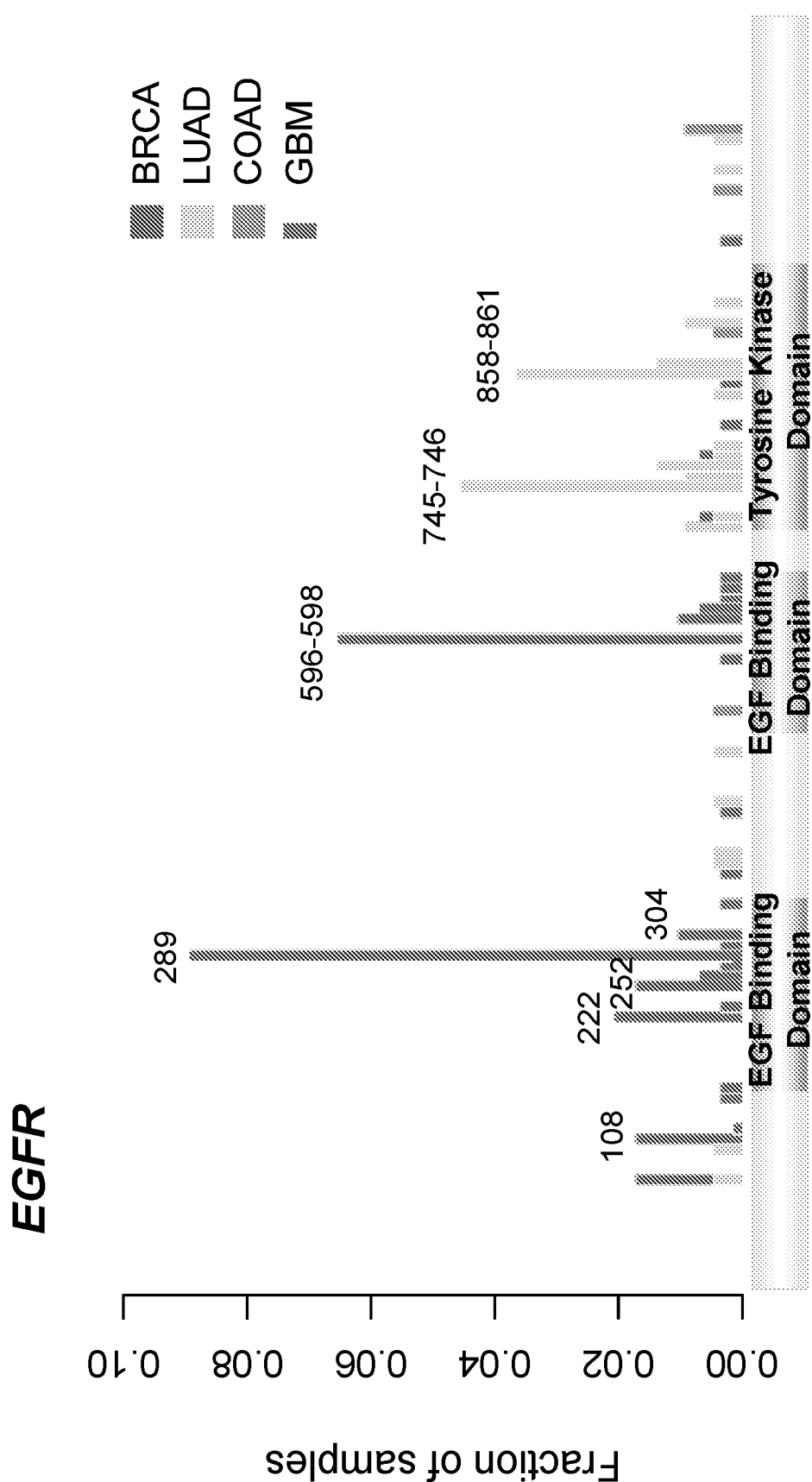
FIG. 9 illustrates mutation hotspots in Epidermal Growth Factor Receptors (EGFRs) across different types of cancer.
Figures 10A, 10B:
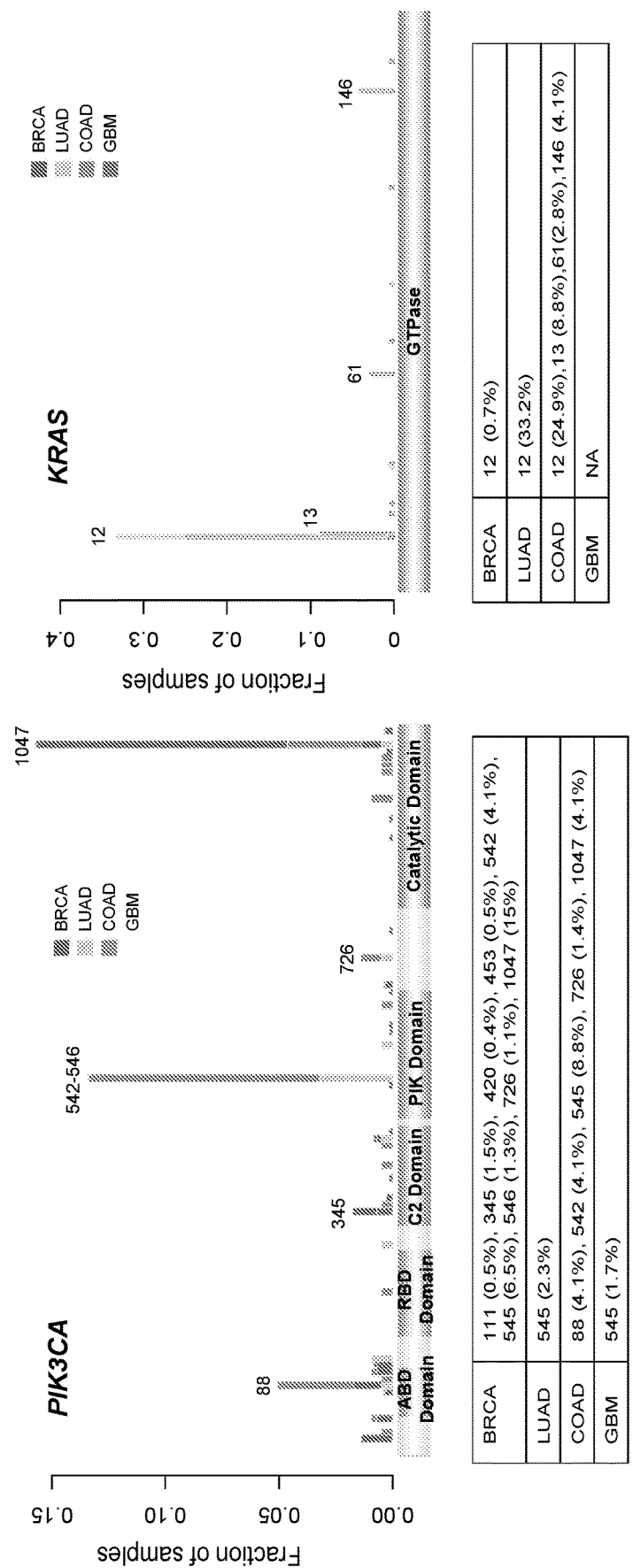
FIG. 10A illustrates mutational hotspots in KRAS across different types of cancer.
FIG. 10B illustrates mutational hotspots in KRAS across different types of cancer.

FIGS. 8, 9, 10A, and 10B illustrate the difference of oncogenes across tumor types. FIG. 8 illustrates the top 20 oncogenes detected in the four cancer types. The identified oncogenes (OGs) are those with significant spatial clustering on proteins. FIG. 8 shows that the predicted OGs are different for different types of cancer. Most oncogenes are specific to a given cancer type, and only 5 oncogenes are shared across the four cancer types, as shown in FIG. 8. The mutation hotspots identified on these 5 genes are examined in detail as shown in FIGS. 9, 10A, and 10B.

FIG. 9 illustrates mutation hotspots in Epidermal Growth Factor Receptors (EGFRs) across different types of cancer. Although significantly mutated in both LUAD and GBM, the mutational hotspots in EGFR are different for LUAD and GBM as shown in FIG. 9. The mutations for GBM occur mostly in the EGF-binding domain (the extra-cellular domain), whereas the mutations for LUAD cluster in the tyrosine kinase domain (the intra-cellular domain). Therefore, mutations for GBM and mutations for LUAD may have different responses to EGFR inhibition drugs, as described in Vivanco et al., "*Differential sensitivity of glioma-versus lung cancer-specific EGFR mutations to EGFR kinase inhibitors*," Cancer Discov., 2, 458-71 (2012).

FIG. 10A illustrates mutational hotspots in PIK3CA across different types of cancer. FIG. 10A illustrates mutational hotspots in KRAS across different types of cancer. Each number in the table shown in FIGS. 10A and 10B represents the percentage of samples having mutations at a particular position. Among mutational hotspots in PIK3CA, the most mutated positions are positions 542, 545, and 1047. Positions 542 and 545 are in the PIK domain and position 1047 is in a catalytic domain. The mutations at these positions occur in a mutually exclusive manner across samples. For BRCA and COAD, the Phosphoinositide 3-kinase, accessory (PIK) domain and catalytic domain are highly mutated (~26% and ~17% of all samples, respectively), but only ~2.3% and ~1.7% of samples in LUAD and GBM have mutations in these positions. Position 88 in adaptor binding domain (ABD) is identified as an additional hotspot for COAD. KRAS is hyper-mutated in LUAD and COAD (~33.2% and 41%, respectively), with additional hotspots at positions 13, 61, and 146 discovered in COAD.

F. Highly Disrupted Pathways Vary Across Samples

Mutations in genes involved in the same pathway may trigger a similar oncogenic process. The method disclosed herein can be used to detect significantly enriched pathways. To detect disrupted pathways, both cross-samples and within-sample mutation significances are tested. For cross-samples analysis, a pathway is considered significantly mutated if any gene in the pathway is significantly mutated, and whether the pathway is disrupted in multiple samples compared to the background is then tested. For within-sample analysis, whether genes in the pathway are hyper-mutated is analyzed. Highly mutated pathways are generally involved in apoptosis or signaling pathways, which are shown in FIG. 11. BRCA pathway enrichment analysis results using pathways in other pathway databases are shown in FIG. 12.

Figure 13:
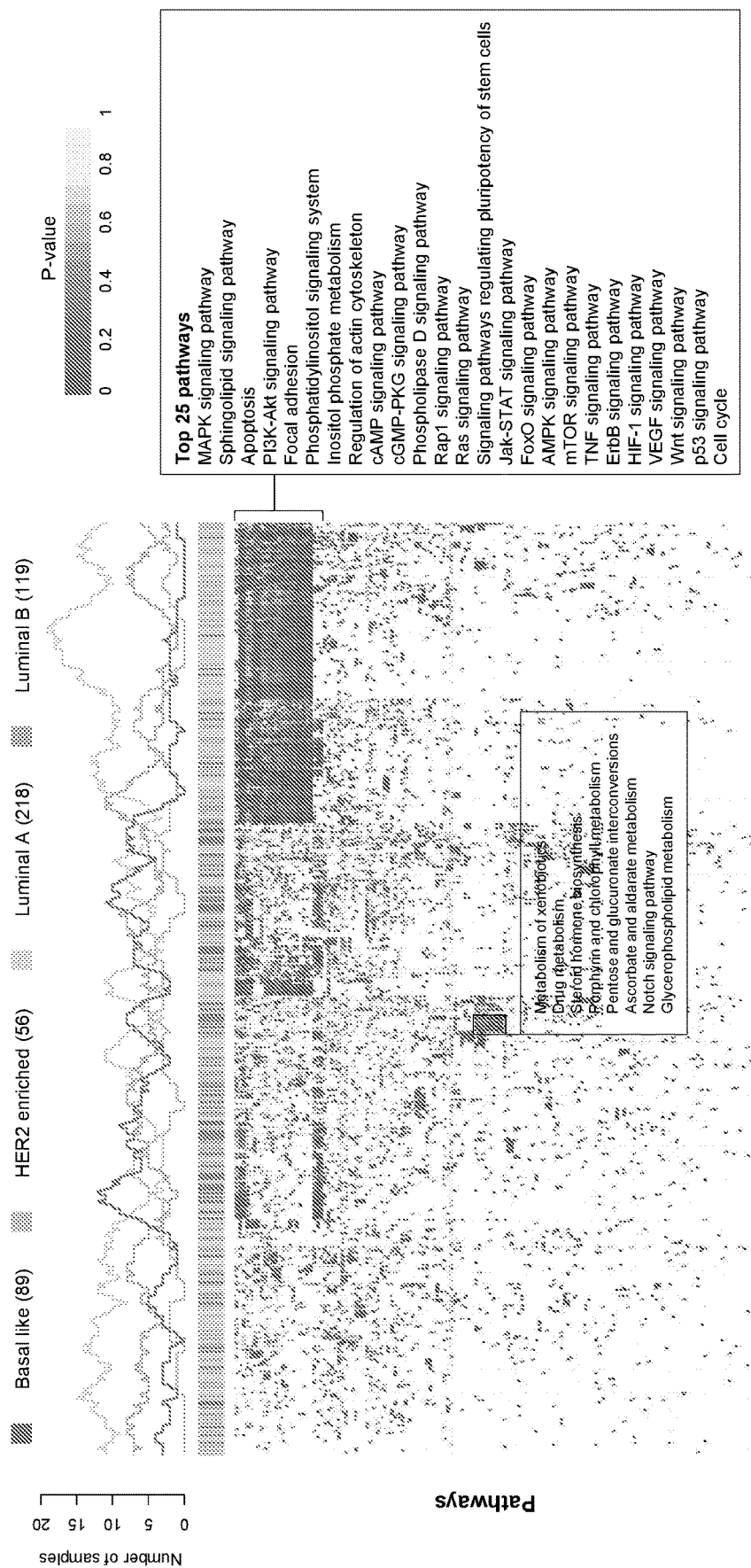
FIG. 13 illustrates pathway enrichment analysis in BRCA using Kyoto Encyclopedia of Genes and Genomes (KEGG) pathways.

FIG. 13 illustrates pathway enrichment analysis in breast cancer cohort (BRCA). In the bottom heatmap, the rows correspond to KEGG (http://www.genome.jp/kegg/) pathways (from Hoadley et al.), the columns correspond to tumor samples, and the color reflects the p-value. The middle bar indicates the tumor subtypes. The top plot shows the number of samples belonging to each subtype within a 20-sample sliding window of the heatmap. Pathways that are disrupted in a large fraction of samples are apoptosis, phosphorylation, and cell adhesion related. These pathways are mostly mutated in Luminal A subtype. Some samples demonstrate a unique disruptive pattern of pathways. The group of samples indicated in the black rectangle in FIG. 13 is highly mutated in a subset of metabolic pathways.

G. Comparison of Breast Cancer Samples from Two Independent Studies

The whole genome sequenced breast cancer samples from Nik-Zainal et al. are obtained, and samples with matched clinical status are selected from the whole genome sequenced breast cancer samples to evaluate the consistency between different datasets.

Figure 14A:
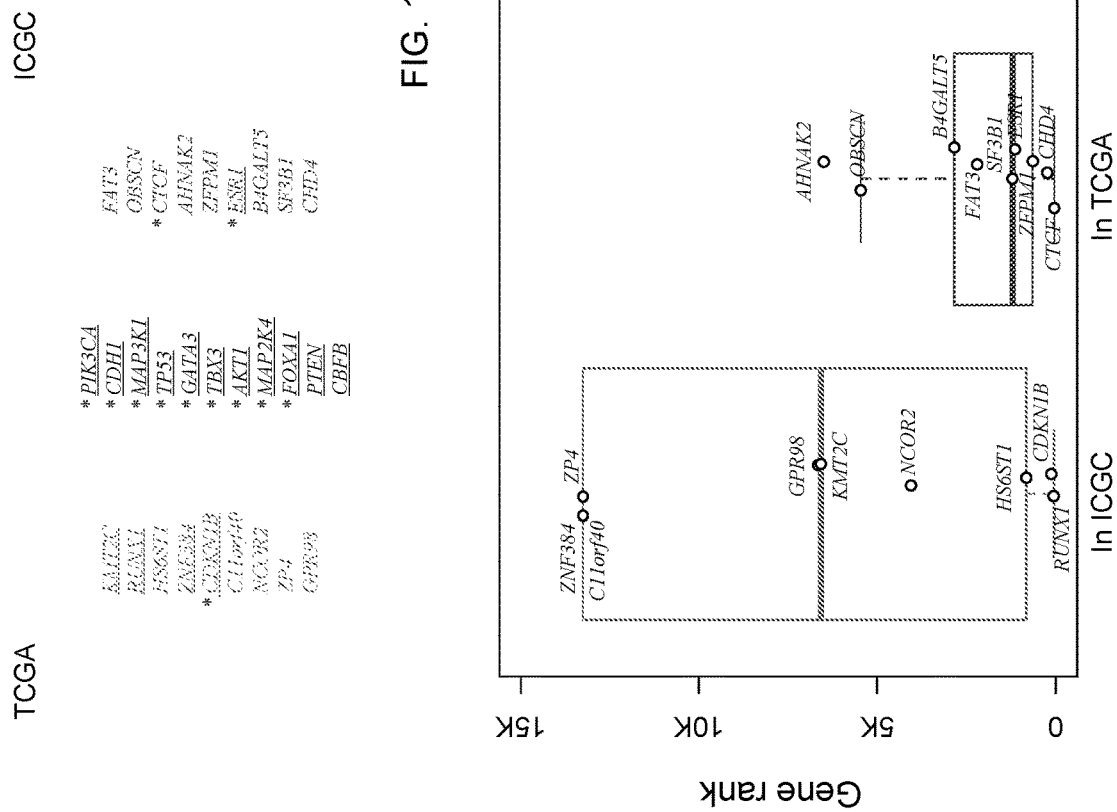
FIGS. 14A-14C illustrate the comparison of breast tumor samples from The Cancer Genome Atlas (TCGA) and the International Cancer Genome Consortium (ICGC).
Figure 14B:
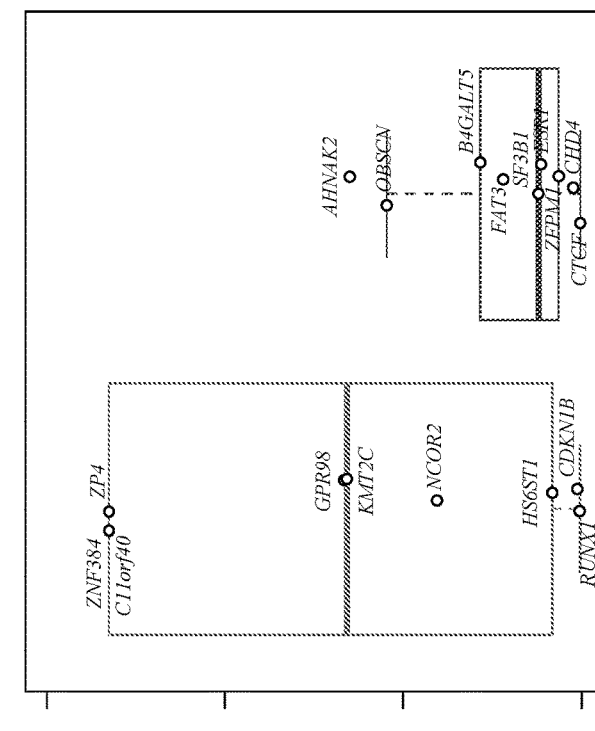
Figure 14C:
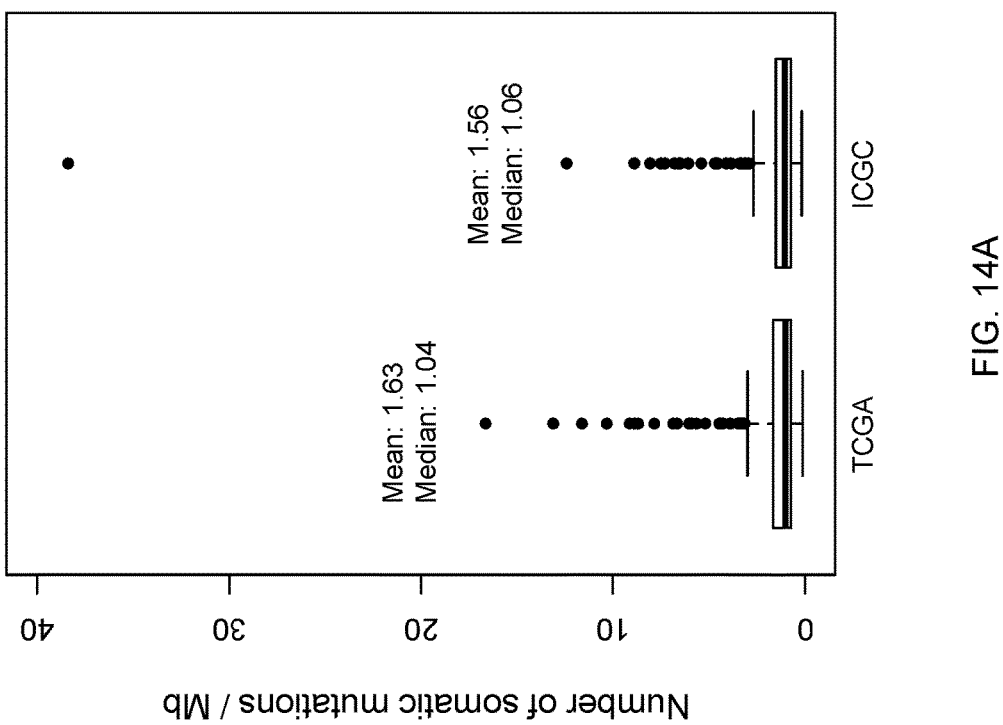

FIGS. 14A-14C illustrate the comparison of breast tumor samples from TCGA and ICGC. FIG. 14A illustrates the average number of somatic mutations per Mb in the exome per sample. FIG. 14B illustrates the intersection of the top 20 genes from ICGC and TCGA. Genes in CGC are underlined. Known breast cancer genes are marked as *. FIG. 14C illustrates the gene rank (by p-values) of non-overlapping genes shown in FIG. 14B in the opposite dataset. As shown in FIG. 14A, the average number of mutations per Mb in the exome is similar (1.63 and 1.56) and the driver gene rankings are correlated (p-value <2.2e-16; spearman correlation: 0.15) in the two datasets. As shown in FIG. 14B, of the top 20 genes for each dataset, the 11 shared genes are known cancer drivers. Examining the specific genes identified in each dataset reveals that genes discovered with ICGC calls generally rank low in the result of TCGA calls, whereas genes discovered with TCGA calls generally rank higher with ICGC calls. This suggests that ICGC results are more consistent than other datasets, such as TCGA data.

H. Oncological Insights from Lung Adenocarcinoma and Lung Squamous Cell Carcinoma Somatic mutations from 569 lung adenocarcinoma (LUAD) samples and 490 lung squamous cell carcinoma (LUSC) samples are determined using the method of SomaticSeq (Fang et al.). Mutation frequencies for hyper-mutated genes are similar and consistent with previous studies conducted on smaller datasets (publications from Cancer Genome Atlas Research Network).

Figure 15B:
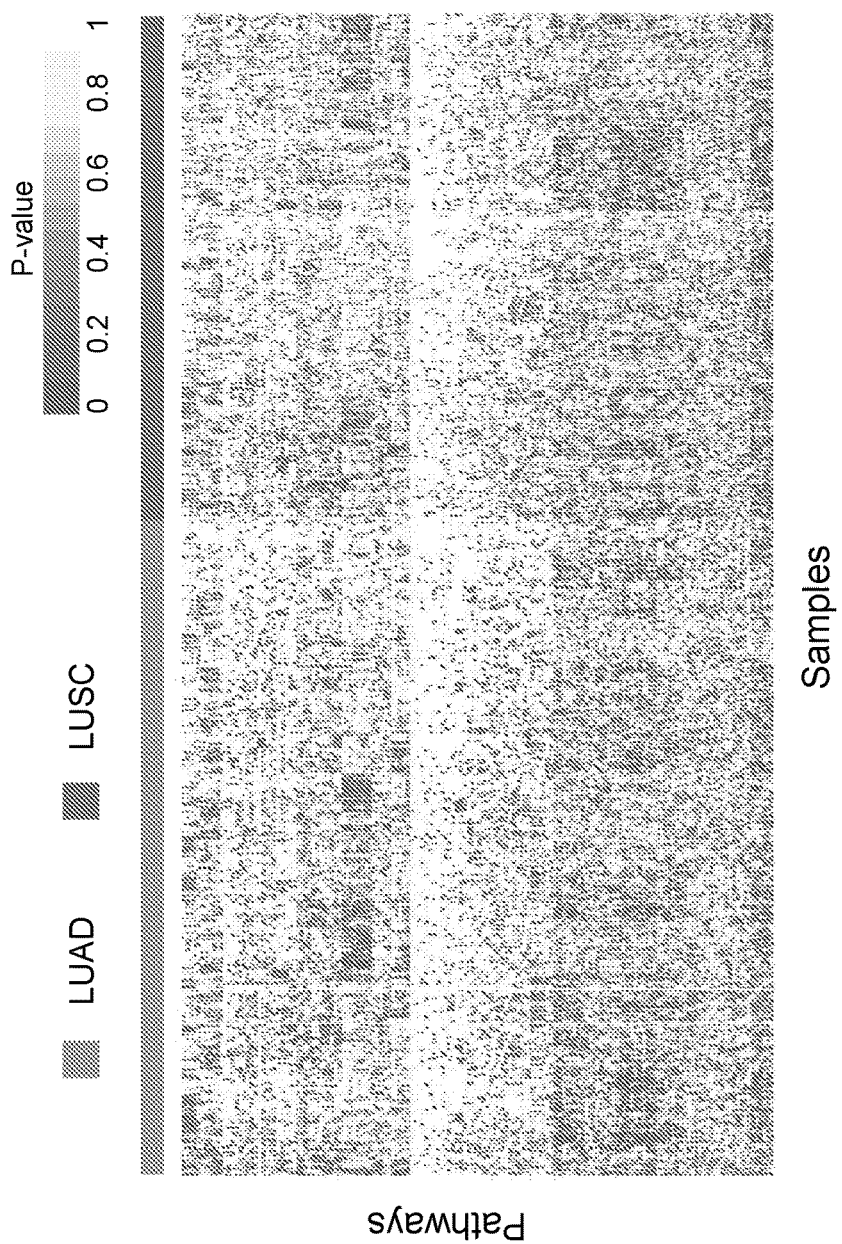
FIG. 15B illustrates the pathway disruption pattern in LUAD and LUSC.
Figure 15A:
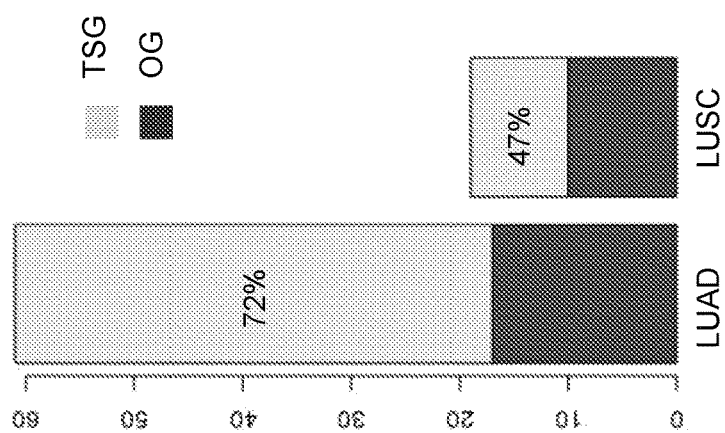
FIG. 15A illustrates the number of discovered tumor suppressor genes and oncogenes in lung adenocarcinoma (LUAD) and lung squamous cell carcinoma (LUSC).

FIG. 15A illustrates the number of discovered tumor suppressor genes and oncogenes in LUAD and LUSC. The LUAD and LUSC samples have a median of 578 and 696 mutations, respectively. For driver genes that could be classified as TSGs and OGs, a much higher fraction of genes are TSGs for LUAD samples compared with the fraction of genes that are TSGs for LUSC samples (72% vs. 47%).

FIG. 15B illustrates the pathway disruption pattern for LUAD and LUSC. FIG. 15B shows that the pathway disruption pattern is similar among lung cancer, whereas there is a clear distinction across breast cancer subtypes as shown by FIG. 13.

Figure 16:
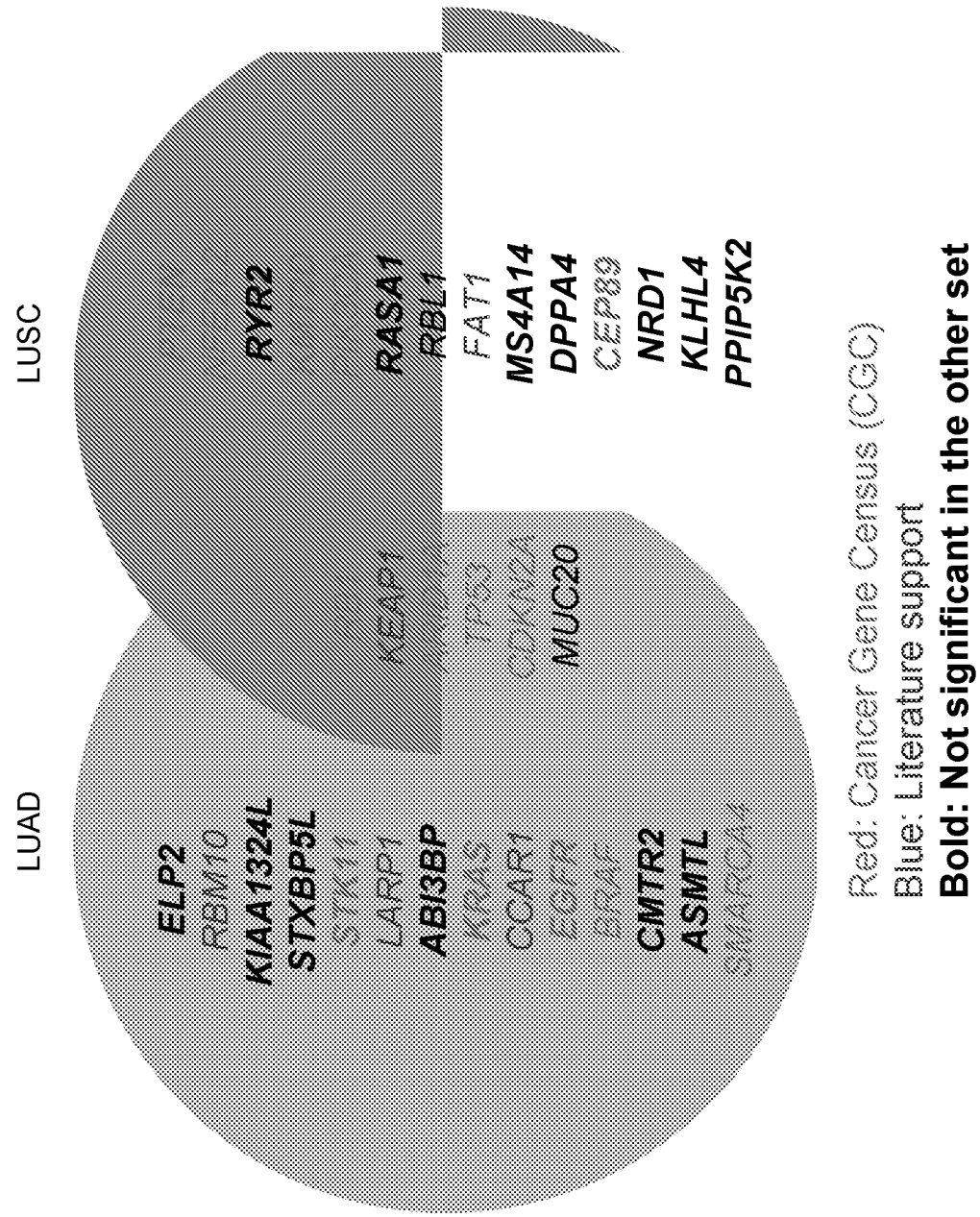
FIG. 16 illustrates the overlapping of top 20 driver genes in LUAD and LUSC.

FIG. 16 illustrates the overlapping of top 20 driver genes for LUAD and LUSC. 97 and 50 potential driver genes has been identified for LUAD and LUSC, respectively. In FIG. 16, a gene labeled in red means that the gene has been reported in Cancer Gene Census database (but not necessarily for lung cancer). A gene labeled in blue means that the gene has been suggested in literature as cancer-related (but majority of them are not suggested as related to lung cancer). Genes labeled in black, such as MUC20, ELP2, and RYR2, are genes identified by the techniques first described in the present disclosure. Genes labeled in bold are genes that are significant for one of LUAD and LUSC, but not both. FIG. 16 shows that only 6 genes (TP53, KEAP1, CDKN2A, MUC20, RB1, and ARID1A) are common for LUAD and LUSC. A novel driver for lung cancer that has not been described in any literature, MUC20, is identified using the method described in this disclosure. MUC20 encodes a cell surface protein, and its overexpression could enhance migration and invasion abilities of colorectal cancer cells (Xiao et al.). The analysis results also show that missense mutations mostly occur at position 3 and 671 on MUC20 in both LUAD and LUSC, whereas in-frame deletions are only at position 12 in LUAD.

IX. DIAGNOSTIC ASSAY AND TREATMENT

A. Detection of Mutations or Variations Associated with Cancer

Embodiments also provide methods for the diagnosis or prognosis of cancer in a subject by detecting the presence in a sample from the subject of one or more somatic mutations or variations associated with cancer as identified by techniques disclosed herein. For example, once genes with more mutations than expected are identified, these genes can be determined to be potentially leading to the cancer. The mutations identified in the genes can be detected in a diagnostic assay. The assay can be created in a variety of ways and use various techniques, such as PCR, sequencing, or hybridization arrays. In various embodiments, the somatic mutation is a substitution, an insertion, or a deletion in the gene.

In an embodiment, a method can detect the presence or absence of a somatic mutation indicative of cancer in a subject, comprising: (a) contacting a sample from the subject with a reagent capable of detecting the presence or absence of a somatic mutation identified as described herein; and (b) determining the presence or absence of the mutation, wherein the presence of the mutation indicates that the subject is afflicted with, or at risk of developing, cancer. The reagent for use in the method may be an oligonucleotide, a DNA probe, an RNA probe, and a ribozyme. In some embodiments, the reagent is labeled. Labels may include, for example, radioisotope labels, fluorescent labels, bioluminescent labels or enzymatic labels.

Mutations in a gene or gene product can be detected in tumors or other body samples such as urine, sputum or blood or blood serum. The same techniques discussed above for detection of mutation in a gene or gene product in tumor samples can be applied to other body samples. For example, cancer cells are sloughed off from tumors and appear in such body samples. State of the art nucleic acid detection methods are capable of detecting mutant cells in a background of non-tumor cells in a wide variety of sample types.

Multiple mutations can be detected simultaneously or separately by using hybridization to multiple probes, for example in a dot-blot or nucleic acid array format, multiplex PCR, for example multiplex allele-specific PCR and multiplex PCR followed by a probe melting assay with each probe characterized by a mutation-specific melting temperature. Multiple mutations may also be detected by nucleic acid sequencing. Multiple samples can be conveniently analyzed using high-throughput sequencing for example, using a method involving emulsion PCR amplification of single molecules adhered to a solid support, subsequent sequencing by synthesis and bioinformatic analysis of the sequence data, such as the method developed by 454 Life Sciences, Inc. (Branford, Conn.) or alternative high-throughput sequencing methods and devices, e.g., ION PROTON® and PGM™, Life Technologies, Grand Island, N.Y.; HISEQ® and MISEQ®, Illumina, San Diego, Calif.).

In yet another embodiment, a kit can contain reagents necessary for detecting one or more mutations. The kit may comprise oligonucleotides such as probes and amplification primers specific for the mutated sequence but not the wild type sequence. In some embodiments, the kit further comprises reagents necessary for the performance of amplification and detection assay, such as the components of PCR, a real-time PCR, or transcription mediated amplification (TMA). In some embodiments, the mutation-specific oligonucleotide is detectably labeled. In such embodiments, the kit comprises reagents for labeling and detecting the label. For example, if the oligonucleotide is labeled with biotin, the kit may comprise a streptavidin reagent with an enzyme and its chromogenic substrate.

Some embodiments described herein may be performed by a computer program that comprises a computer executable logic that is recorded on a computer readable medium. For example, the computer program can execute some or all of the following functions: (i) controlling isolation of nucleic acids from a sample, (ii) pre-amplifying nucleic acids from the sample or (iii) selecting, amplifying, sequencing or arraying specific regions in the sample, (iv) identifying and quantifying somatic mutations in a sample, (v) comparing data on somatic mutations detected from the sample with a predetermined threshold, (vi) determining the tumor load based on the presence of somatic mutations in circulating free DNA, and (vii) declaring an assessment of tumor load, residual disease, response to therapy, or initial diagnosis.

Once detected to have one or more mutations associated with cancer, the patient can be administered a compound that inhibits signaling of the mutant protein encoded by the mutated gene. In an embodiment, the presence of a first somatic mutation together with the presence of at least one additional somatic mutation is indicative of an increased risk of cancer compared to a subject having the first somatic mutation and lacking the presence of the at least one additional somatic mutation.

A therapeutic agent for the treatment of cancer may be incorporated into compositions, which in some embodiments are suitable for pharmaceutical use. Such compositions typically comprise the peptide or polypeptide, and an acceptable carrier, for example one that is pharmaceutically acceptable. A "pharmaceutically acceptable carrier" includes any and all solvents, dispersion media, coatings, antibacterial and antifungal agents, isotonic and absorption delaying agents, and the like, compatible with pharmaceutical administration. Examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions. A therapeutic agent (and any additional therapeutic agent for the treatment of cancer) can be administered by any suitable means, including parenteral, intrapulmonary, intrathecal and intranasal, and, if desired for local treatment, intralesional administration. Parenteral infusions include, e.g., intramuscular, intravenous, intra-arterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

B. Detection of Genes Associated with Lung Cancer

In another aspect, methods for the detection, diagnosis, and/or treatment of a lung cancer are provided herein. In some embodiments, a method of detecting a lung cancer is provided. In some embodiments, a method of diagnosing a subject as having a lung cancer is provided. In some embodiments, the method comprises:

detecting in a sample from the subject one or more (e.g., 1, 2, 3, 4, 5, 6, 7, 8, 9, 10, 15, 20 or more) mutations in one or more (e.g., 1, 2, 3, 4, 5, 6, 7, 8, 9, 10 or more) genes selected from the group consisting of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2;

wherein the presence of one or more mutations in the one or more genes identifies the subject as having lung cancer.

In some embodiments, the method comprises detecting in a sample from the subject one or more (e.g., 1, 2, 3, 4, 5, 6, 7, 8, 9, 10, 15, 20 or more) somatic and/or germline mutations in one or more genes as described herein. In some embodiments, the method comprises detecting in a sample from the subject one or more (e.g., 1, 2, 3, 4, 5, 6, 7, 8, 9, 10, 15, 20 or more) somatic mutations in one or more genes as described herein. In some embodiments, the mutation is a point mutation, insertion mutation, deletion mutation, or truncation mutation. In some embodiments, the mutation is an activation mutation. In some embodiments, the mutation is a loss-of-function mutation.

In some embodiments, the lung cancer is non-small cell lung cancer. In some embodiments, the lung cancer is adenocarcinoma, squamous cell carcinoma, or large cell carcinoma. In some embodiments, the lung cancer is lung squamous cell carcinoma. In some embodiments, the lung cancer is lung adenocarcinoma. In some embodiments, the lung cancer is small cell lung cancer.

In some embodiments, the method comprises: detecting in a sample from the subject one or more (e.g., 1, 2, 3, 4, 5, 6, 7, 8, 9, 10, 15, 20 or more) mutations in one or more (e.g., 1, 2, 3, 4, 5, 6, 7, 8, 9, 10 or more) genes selected from the group consisting of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, and MUC20; wherein the presence of one or more mutations in the one or more genes identifies the subject as having lung cancer. In some embodiments, the presence of one or more mutations in one or more genes selected from the group consisting of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, and MUC20 identifies the subject as having lung adenocarcinoma. In some embodiments, the method comprises detecting in a sample from the subject one or more mutations in one or more of ELP2, KIAA1324L, STXBP5L, ABI3BP, CMTR2, ASMTL, or MUC20. In some embodiments, the method comprises detecting in a sample from the subject one or more mutations in each of ELP2, KIAA1324L, STXBP5L, ABI3BP, CMTR2, ASMTL, and MUC20.

In some embodiments, the method comprises: detecting in a sample from the subject one or more (e.g., 1, 2, 3, 4, 5, 6, 7, 8, 9, 10, 15, 20 or more) mutations in one or more (e.g., 1, 2, 3, 4, 5, 6, 7, 8, 9, 10 or more) genes selected from the group consisting of RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2; wherein the presence of one or more mutations in the one or more genes identifies the subject as having lung cancer. In some embodiments, the presence of one or more mutations in one or more genes selected from the group consisting of RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2 identifies the subject as having lung squamous cell carcinoma. In some embodiments, the method comprises detecting in a sample from the subject one or more mutations in one or more of MUC20, RYR2, RASA1, RBL1, MS4A14, DPPA4, NRD1, KLHL4, or PPIP5K2. In some embodiments, the method comprises detecting in a sample from the subject one or more mutations in each of MUC20, RYR2, RASA1, RBL1, MS4A14, DPPA4, NRD1, KLHL4, and PPIP5K2.

In some embodiments, the method comprises detecting in a sample from the subject one or more (e.g., 1, 2, 3, 4, 5, 6, 7, 8, 9, 10, 15, 20 or more) mutations in one or more (e.g., 1, 2, 3, 4, 5, 6, 7, 8, 9, 10 or more) genes selected from the group consisting of RB1, KEAP1, ARID1A, TP53, CDKN2A, and MUC20; wherein the presence of one or more mutations in the one or more genes identifies the subject as having lung cancer. In some embodiments, the method comprises detecting the presence of one or more mutations in MUC20; wherein the presence of one or more mutations in MUC20 identifies the subject as having lung cancer (e.g., lung adenocarcinoma or lung squamous cell carcinoma).

In some embodiments, the method comprises detecting in a sample from the subject one or more (e.g., 1, 2, 3, 4, 5, 6, 7, 8, 9, 10, 15, 20 or more) mutations in one or more genes selected from the group consisting of ELP2, KIAA1324L, STXBP5L, ABI3BP, CMTR2, ASMTL, MUC20, RYR2, RASA1, RBL1, MS4A14, DPPA4, NRD1, KLHL4, and PPIP5K2.

In some embodiments, the method comprises:
detecting in a sample from the subject one or more (e.g., 1, 2, 3, 4, 5, 6, 7, 8, 9, 10, 15, 20 or more) mutations in one or more genes selected from the group consisting of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2; and
comparing the number of mutations detected in the one or more genes in the sample from the subject to a reference value;
wherein an increased number of mutations in the one or more genes in the sample from the subject, as compared to the reference value, identifies the subject as having lung cancer. In some embodiments, the genes are selected from the group consisting of ELP2, KIAA1324L, STXBP5L, ABI3BP, CMTR2, ASMTL, MUC20, RYR2, RASA1, RBL1, MS4A14, DPPA4, NRD1, KLHL4, and PPIP5K2.

In some embodiments, the method comprises:
detecting in a sample from the subject one or more (e.g., 1, 2, 3, 4, 5, 6, 7, 8, 9, 10, 15, 20 or more) mutations in one or more genes selected from the group consisting of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, and MUC20; and comparing the number of mutations detected in the one or more genes in the sample from the subject to a reference value;

wherein an increased number of mutations in the one or more genes in the sample from the subject, as compared to the reference value, identifies the subject as having lung cancer. In some embodiments, the method comprises detecting the number of mutations in one or more genes selected from the group consisting of ELP2, KIAA1324L, STXBP5L, ABI3BP, CMTR2, ASMTL, and MUC20, and comparing the number of mutations in the one or more genes to a reference value. In some embodiments, the method comprises detecting in a sample from the subject one or more mutations in each of ELP2, KIAA1324L, STXBP5L, ABI3BP, CMTR2, ASMTL, and MUC20, and comparing the number of mutations detected in each of the genes to a reference value. In some embodiments, the lung cancer is lung adenocarcinoma.

In some embodiments, the method comprises:

detecting in a sample from the subject one or more (e.g., 1, 2, 3, 4, 5, 6, 7, 8, 9, 10, 15, 20 or more) mutations in one or more genes selected from the group consisting of RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2; and comparing the number of mutations detected in the one or more genes in the sample from the subject to a reference value;

wherein an increased number of mutations in the one or more genes in the sample from the subject, as compared to the reference value, identifies the subject as having lung cancer. In some embodiments, the method comprises detecting the number of mutations in one or more genes selected from the group consisting of MUC20, RYR2, RASA1, RBL1, MS4A14, DPPA4, NRD1, KLHL4, and PPIP5K2, and comparing the number of mutations detected in the one or more genes to a reference value. In some embodiments, the method comprises detecting in a sample from the subject one or more mutations in each of MUC20, RYR2, RASA1, RBL1, MS4A14, DPPA4, NRD1, KLHL4, and PPIP5K2, and comparing the number of mutations detected in each of the genes to a reference value. In some embodiments, the lung cancer is lung squamous cell carcinoma.

In some embodiments, the method comprises:

detecting in a sample from the subject one or more (e.g., 1, 2, 3, 4, 5, 6, 7, 8, 9, 10, 15, 20 or more) mutations in one or more genes selected from the group consisting of RB1, KEAP1, ARID1A, TP53, CDKN2A, and MUC20; and comparing the number of mutations detected in the one or more genes in the sample from the subject to a reference value;

wherein an increased number of mutations in the one or more genes in the sample from the subject, as compared to the reference value, identifies the subject as having lung cancer. In some embodiments, the method comprises detecting the presence of one or more mutations in MUC20 and comparing the number of mutations in MUC20 to a reference value. In some embodiments, the method comprises detecting in a sample from the subject one or more mutations in each of RB1, KEAP1, ARID1A, TP53, CDKN2A, and MUC20, and comparing the number of mutations detected in each of the genes to a reference value.

In some embodiments, the reference value for a particular gene is a background mutation rate as described herein. In some embodiments, the reference value for a gene is determined for a control subject or population of subjects (e.g., 10, 20, 50, 100, 200, 500 subjects or more) known to be negative for cancer (e.g., lung cancer). In some embodiments, the control subject or population of subjects is matched to a test subject according to one or more characteristics such as age, sex, ethnicity, or other criteria. In some embodiments, the reference value is established using the same type of sample from the control subject or population of subjects (e.g., a sample comprising blood or a tumor tissue sample) as is used for detecting the presence of mutations in the test subject.

The wild-type gene sequences of ELP2, RBM10, KIAA1324L, STXBP5L, STK11, LARP1, ABI3BP, KRAS, CCAR1, EGFR, BRAF, CMTR2, ASMTL, SMARCA4, RB1, KEAP1, ARID1A, TP53, CDKN2A, MUC20, PTEN, NFE2L2, RYR2, KMT2D, PIK3CA, RASA1, RBL1, FAT1, MS4A14, DPPA4, CEP89, NRD1, KLHL4, and PPIP5K2 are known in the art and are disclosed, e.g., in the Genbank sequence database as follows: ELP2 (elongator acetyltransferase complex subunit 2): Genbank Accession No. NM_001242875.2, NM_001242876.2, NM_001242877.2, NM_001242878.2, NM_001242879.2, NM_001324465.1, NM_001324466.1, NM_001324467.1, NM_001324468.1, or NM_018255.3; RBM10 (RNA binding motif protein 10): NM_001204466.1, NM_001204467.1, NM_001204468.1, NM_005676.4, or NM_152856.2; KIAA1324L (KIAA1324 like): NM_001142749.2, NM_001291990.1, NM_001291991.1, or NM 152748.3; STXBP5L (syntaxin binding protein 5 like): NM_001308330.1; STK11 (serine/threonine kinase 11): NM_000455.4; LARP1 (La ribonucleoprotein domain family member 1): NM_015315.4; ABI3BP (ABI family member 3 binding protein): NM_001349329.1, NM_001349440.1, NM_001349331.1, NM_001349332.1, or NM_015429.3; KRAS (KRAS proto-oncogene): NM_004985.4 or NM_033360.3; CCAR1 (cell division cycle and apoptosis regulator 1): NM_001282959.1 or NM_001282960.1); EGFR (epidermal growth factor receptor): NM_001346897.1, NM_001346898.1, NM_001346899.1, NM_001346900.1, NM_001346941.1, NM_005228.4, NM_201282.1, NM_201283.1, or NM_201284.1; BRAF (B-Raf proto-oncogene, serine/threonine kinase): NM_004333.4; CMTR2 (cap methyltransferase 2): NM_001099642.1, NM_001324374.1, NM_001324377.1, NM_001324378.1, NM_001324379.1, or NM_018348.5; ASMTL (acetylserotonin O-methyltransferase like): NM_001173473.1, NM_001173474.1, or NM_004192.3; SMARCA4 (SWI/SNF related, matrix associated, actin dependent regulator of chromatin, subfamily a, member 4): NM_001128849.1; RB1 (RB transcriptional corepressor 1): NM_000321.2; KEAP1 (kelch like ECH associated protein 1): NM_012289.3 or NM_203500.1; ARID1A (AT-rich interaction domain 1A): NM_006015.4 or NM_139135.2; TP53 (tumor protein 53): NM_000546.5, NM_001126112.2, NM_001126113.2, NM_001126114.2, NM_001126115.1, NM_001126116.1, NM_001126117.1, NM_001126118.1, NM_001276695.1, NM_001276696.1, NM_001276697.1, NM_001276698.1, NM_001276699.1, NM_001276760.1, or NM_001276761.1; CDKN2A (cyclin dependent kinase inhibitor 2A): NM_000077.4, NM_001195132.1, NM_058195.3, or NM_058197.4;

MUC20 (mucin 20, cell surface associated): NM_001282506.1, NM_001291833.1, NM_020790.1, or NM_152673.3; PTEN (phosphatase and tensin homolog): NM_000314.6, NM_001304717.2, or NM_001304718.1; NFE2L2 (nuclear factor, erythroid 2 like 2): NM_001145412.3, NM_001145413.3, NM_001313900.1, NM_001313901.1, NM_001313902.1, NM_001313903.1, NM_001313904.1, or NM_006164.4; RYR2 (ryanodine receptor 2): NM_001035.2; KMT2D (lysine methyltransferase 2D): NM_003482.3; PIK3CA (phosphatidylinositol-4,5-bisphosphate 3-kinase catalytic subunit alpha): NM_006218.3; RASA1 (Ras GTPase-activating protein 1): NM_002890.2 or NM_0022650.2; RBL1 (RB transcriptional corepressor like 1): NM_001323281.1, NM_001323282.1, NM_002895.4, or NM_183404.3; FAT1 (FAT atypical cadherin 1): NM_005245.3; MS4A14 (membrane spanning 4-domains A14): NM_001079692.2, NM_001261827.1, NM_001261828.1, or NM_032597.4; DPPA4 (developmental pluripotency associated 4): NM_001348928.1, NM_001348929.1, or NM_018189.3; CEP89 (centrosomal protein 89): NM_032816.4; NRD1 (Nrd1 complex RNA-binding subunit): NM_001183089.1; KLHL4 (kelch like family member 4): NM_019117.4 or NM_057162.2; PPIP5K2 (diphosphoinositol pentakisphosphate kinase 2): NM_001276277.2, NM_001281471.2, NM_001345871.1, NM_001345782.1, NM_001345873.1, NM_001345874.1, NM_001345875.1, NM_001345876.1, NM_001345877.1, NM_001345878.1, or NM_015216.4. In some embodiments, the methods comprise detecting one or more mutations in one or more of the wild-type sequences disclosed herein.

Analysis of nucleic acid expression levels or genotypes can be performed using techniques known in the art, such as but not limited to microarrays, polymerase chain reaction (PCR)-based analysis, sequence analysis, electrophoretic analysis, Southern analysis, reverse-transcriptase polymerase chain reaction (RT-PCR), Real-Time reverse transcription PCR (Real-Time RT-PCR), semi-quantitative RT-PCR, quantitative PCR (qPCR), quantitative RT-PCR (qRT-PCR), or multiplexed branched DNA (bDNA) assay. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), sequencing by hybridization (Drmanac et al., *Nature Biotech.*, 16:54-58 (1998), and "next generation sequencing" methods, including but not limited to sequencing by synthesis (e.g., HiSeq™, MiSeq™, or Genome Analyzer, each available from Illumina), sequencing by ligation (e.g., SOLID™, Life Technologies), ion semiconductor sequencing (e.g., Ion Torrent™, Life Technologies), pyrosequencing (e.g., 454™ sequencing, Roche Diagnostics), and RNA sequencing. See, e.g., Liu et al., *J. Biomed Biotechnol*, 2012, 2012:251364. Non-limiting examples of electrophoretic analysis include slab gel electrophoresis such as agarose or polyacrylamide gel electrophoresis, capillary electrophoresis, and denaturing gradient gel electrophoresis. In some embodiments, methods for detecting nucleic acid mutations or variations include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE), and pyrosequencing.

A detectable moiety can be used in the assays described herein. A wide variety of detectable moieties can be used, with the choice of label depending on the sensitivity required, ease of conjugation with the probe, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

The analysis can be carried out in a variety of physical formats. For example, the use of microtiter plates or automation can be used to facilitate the processing of large numbers of test samples.

In some embodiments, the sample from the subject comprises whole blood, serum, plasma, saliva, urine, cerebrospinal fluid, or a tissue sample (e.g., lung tissue). In some embodiments, the sample comprises a cancer cell (e.g., a cell obtained or derived from a tumor). In some embodiments, the sample comprises a tumor tissue sample.

In some embodiments, subsequent to the step of identifying a subject as having lung cancer, the method further comprises administering one or more therapeutic agents to the subject. In some embodiments, the method comprises administering a chemotherapeutic agent. In some embodiments, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel).

The route of administration of a therapeutic agent can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art. In some embodiments, the therapeutic agent is administered orally, intravenously, or intraperitoneally. In some embodiments, the therapeutic agent is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is within the capability of those skilled in the art.

In some embodiments, a therapeutic agent is administered to the subject over an extended period of time, e.g., for at least 30, 40, 50, 60, 70, 80, 90, 100, 150, 200, 250, 300, 350 day or longer.

X. COMPUTER SYSTEM

Figure 17:
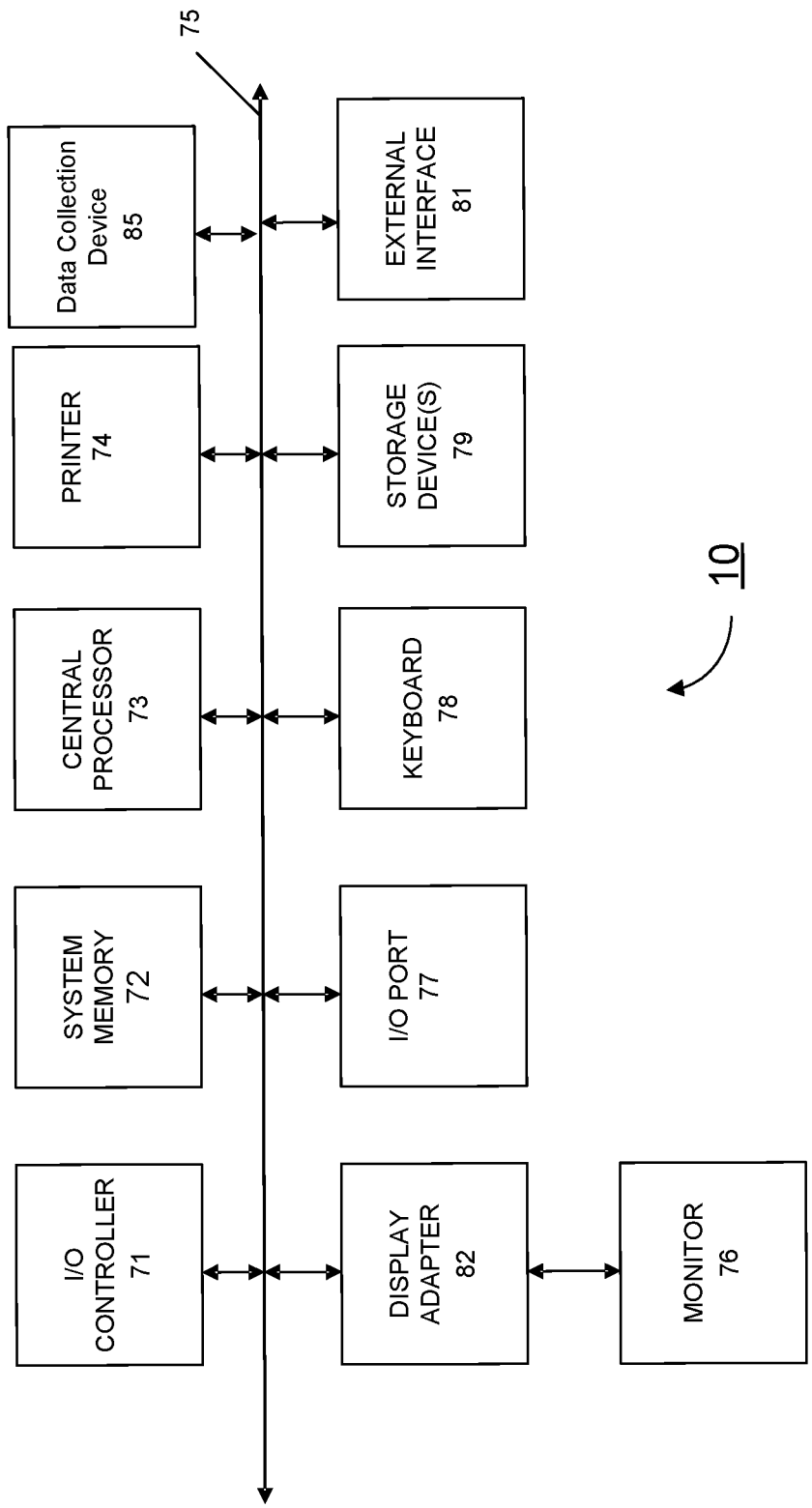
FIG. 17 illustrates an example computer system that may be utilized to implement techniques disclosed herein.

Any of the computer systems mentioned herein may utilize any suitable number of subsystems. Examples of such subsystems are shown in FIG. 17 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 17 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, Fire Wire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

XI. REFERENCES

1. Forbes, S. A., Beare, D., Gunasekaran, P., Leung, K., Bindal, N., Boutselakis, H., Ding, M., Bamford, S., Cole, C., Ward, S., et al. (2015) COSMIC: exploring the world's knowledge of somatic mutations in human cancer. *Nucleic Acids Res.*, 43, D805-11
2. Tamborero, D., Gonzalez-Perez, A. and Lopez-Bigas, N. (2013) OncodriveCLUST: exploiting the positional clustering of somatic mutations to identify cancer genes. *Bioinformatics*, 29, 2238-44.
3. Gonzalez-Perez, A. and Lopez-Bigas, N. (2012) Functional impact bias reveals cancer drivers. *Nucleic Acids Res.*, 40, e169.
4. Lawrence, M. S., Stojanov, P., Polak, P., Kryukov, G. V., Cibulskis, K., Sivachenko, A., Carter, S. L., Stewart, C., Mermel, C. H., Roberts, S. A., et al. (2013) Mutational heterogeneity in cancer and the search for new cancer-associated genes. *Nature*, 499, 214-218.
5. Korthauer, K. D. and Kendziorski, C. (2015) MADGiC: a model-based approach for identifying driver genes in cancer. *Bioinformatics*, 31, 1526-35.
6. Youn, A. and Simon, R. (2011) Identifying cancer driver genes in tumor genome sequencing studies. *Bioinformatics*, 27, 175-81.
7. Van den Eynden, J., Fierro, A. C., Verbeke, L. P., Marchal, K., Vogelstein, β., Papadopoulos, N., Velculescu, Zhou, S., Diaz, L., Kinzler, K., et al. (2015) SomInaClust: detection of cancer genes based on somatic mutation patterns of inactivation and clustering. *BMC Bioinformatics*, 16, 125.
8. Dees, N. D., Zhang, Q., Kandoth, C., Wendl, M. C., Schierding, W., Koboldt, D. C., Mooney, T. B., Callaway, M. B., Dooling, D., Mardis, E. R., et al. (2012) MuSiC: Identifying mutational significance in cancer genomes. *Genome Res.*, 22, 1589-1598.
9. Wendl, M. C., Wallis, J. W., Lin, L., Kandoth, C., Mardis, E. R., Wilson, R. K. and Ding, L. (2011) PathScan: a tool for discerning mutational significance in groups of putative cancer genes. *Bioinformatics*, 27, 1595-602.
10. Alexandrov, L. B., Nik-Zainal, S., Wedge, D. C., Aparicio, S. A. J. R., Behjati, S., Biankin, A. V., Bignell, G. R., Bolli, N., Borg, A., Børresen-Dale, A.-L., et al. (2013) Signatures of mutational processes in human cancer. *Nature*, 500, 415-421.
11. Futreal, P. A., Coin, L., Marshall, M., Down, T., Hubbard, T., Wooster, R., Rahman, N. and Stratton, M. R. (2004) A census of human cancer genes. *Nat. Rev. Cancer*, 4, 177-183.
12. Vivanco, I., Robins, H. I., Rohle, D., Campos, C., Grommes, C., Nghiemphu, P. L., Kubek, S., Oldrini, B., Chheda, M. G., Yannuzzi, N., et al. (2012) Differential sensitivity of glioma-versus lung cancer-specific EGFR mutations to EGFR kinase inhibitors. *Cancer Discov.*, 2, 458-71.
13. Fang, L. T., Afshar, P. T., Chhibber, A., Mohiyuddin, M., Fan, Y., Mu, J. C., Gibeling, G., Barr, S., Asadi, N. B., Gerstein, M. B., et al. (2015) An ensemble approach to accurately detect somatic mutations using SomaticSeq. *Genome Biol.*, 16, 197.
14. Kandoth, C., Mclellan, M. D., Vandin, F., Ye, K., Niu, B., Lu, C., Xie, M., Zhang, Q., McMichael, J. F., Wyczalkowski, M. A., et al. (2013) Mutational landscape and significance across 12 major cancer types. *Nature*, 502, 333-339.
15. Nik-Zainal, S., Davies, H., Staaf, J., Ramakrishna, M., Glodzik, D., Zou, X., Martincorena, I., Alexandrov, L. B., Martin, S., Wedge, D. C., et al. (2016) Landscape of somatic mutations in 560 breast cancer whole-genome sequences. *Nature*, 534, 47-54.
16. McLaren, W., Pritchard, β., Rios, D., Chen, Y., Flicek, P. and Cunningham, F. (2010) Deriving the consequences of genomic variants with the Ensembl API and SNP Effect Predictor. *Bioinformatics*, 26, 2069-70.
17. Hoadley, K. A., Yau, C., Wolf, D. M., Cherniack, A. D., Tamborero, D., Ng, S., Leiserson, M. D. M., Niu, β., McLellan, M. D., Uzunangelov, V., et al. (2014) Multi-platform Analysis of 12 Cancer Types Reveals Molecular Classification within and across Tissues of Origin. *Cell*, 158, 929-944.
18. Caspi, R., Billington, R., Ferrer, L., Foerster, H., Fulcher, C. A., Keseler, I. M., Kothari, A., Krummenacker, M., Latendresse, M., Mueller, L. A., et al. (2016) The Meta-Cyc database of metabolic pathways and enzymes and the BioCyc collection of pathway/genome databases. *Nucleic Acids Res.*, 44, D471-80.
19. Fabregat, A., Sidiropoulos, K., Garapati, P., Gillespie, M., Hausmann, K., Haw, R., Jassal, B., Jupe, S., Korninger, F., Mckay, S., et al. (2016) The Reactome pathway Knowledgebase. *Nucleic Acids Res.*, 44, D481-7.
20. Schaefer, C. F., Anthony, K., Krupa, S., Buchoff, J., Day, M., Hannay, T. and Buetow, K. H. (2009) PID: the Pathway Interaction Database. *Nucleic Acids Res.*, 37, D674-9.
21. Geer, L. Y., Marchler-Bauer, A., Geer, R. C., Han, L., He, J., He, S., Liu, C., Shi, W. and Bryant, S. H. (2010) The NCBI BioSystems database. *Nucleic Acids Res.*, 38, D492-6.
22. Hong, Y. (2013) On computing the distribution function for the Poisson binomial distribution. *Comput. Stat. Data Anal.*, 59, 41-51.
23. Vogelstein, B., Papadopoulos, N., Velculescu, V. E., Zhou, S., Diaz, L. A. and Kinzler, K. W. (2013) Cancer Genome Landscapes. *Science (80-.).*, 339, 1546-1558.
24. Ng, P. C. and Henikoff, S. (2003) SIFT: Predicting amino acid changes that affect protein function. *Nucleic Acids Res.*, 31, 3812-4.
25. Adzhubei, I., Jordan, D. M. and Sunyaev, S. R. (2013) Predicting functional effect of human missense mutations using PolyPhen-2. *Curr. Protoc. Hum. Genet.*, Chapter 7, Unit7.20.
26. Thorner, A. R., Parker, J. S., Hoadley, K. A. and Perou, C. M. (2010) Potential Tumor Suppressor Role for the c-Myb Oncogene in Luminal Breast Cancer. *PLOS One*, 5, e13073.
27. Janes, K. A. (2011) RUNX1 and its understudied role in breast cancer. *Cell Cycle*, 10, 3461.
28. Koboldt, D. C., Fulton, R. S., Mclellan, M. D., Schmidt, H., Kalicki-Veizer, J., McMichael, J. F., Fulton, L. L., Dooling, D. J., Ding, L., Mardis, E. R., et al. (2012) Comprehensive molecular portraits of human breast tumours. *Nature*, 490, 61-70.
29. Cancer Genome Atlas Research Network, T. C. G. A. R. (2014) Comprehensive molecular profiling of lung adenocarcinoma. *Nature*, 511, 543-50.

30. Cancer Genome Atlas Research Network, T. C. G. A. R. (2012) Comprehensive genomic characterization of squamous cell lung cancers. *Nature,* 489, 519-25.
31. Xiao, X., Wang, L., Wei, P., Chi, Y., Li, D., Wang, Q., Ni, S., Tan, C., Sheng, W., Sun, M., et al. (2013) Role of MUC20 overexpression as a predictor of recurrence and poor outcome in colorectal cancer. *J. Transl. Med.,* 11, 151.

What is claimed is:

1. A method comprising:
    performing whole exome sequencing, by a sequence analytical system, of nucleic acid in each sample of a plurality of samples to obtain sequencing data for each sample, wherein each sample is from a same tumor type, and wherein the sequence analytical system comprises a sample holder, a detector, and a computer system;
    measuring, by the sequence analytical system using the sequencing data, a set of mutations in exons of a plurality of genes in each sample of the plurality of samples, wherein the set of mutations for a subject comprises all mutations detected in the exons of the plurality of genes and provides a total number of mutations measured in the exome of the subject, and wherein the plurality of genes comprises all genes;
    for each sample of the plurality of samples, determining, by the computer system, a sample mutation rate based on the total number of mutations measured in the sample;
    for each mutation context of a plurality of mutation contexts, determining, by the computer system, a context mutation rate based on a first number of mutations identified in the sets of mutations for the mutation context, wherein a mutation context corresponds to a type of substitution or deletion;
    for each gene of the plurality of genes,
        determining, for each sample of the plurality of samples, by the computer system, a second number of silent mutations measured in the gene in the sample;
        determining, by the computer system, an expected silent mutation rate using a sum of context mutation rates of silent mutations in the gene, wherein a silent mutation does not cause a change to an amino acid sequence of a translated protein for the gene;
        determining, by the computer system, a probability distribution of a gene-specific background mutation rate across the plurality of samples for the gene based on the expected silent mutation rate for the gene and the sample mutation rates of the plurality of samples, wherein determining the probability distribution of the gene-specific background mutation rate for the gene includes:
            optimizing, by the computer system, one or more parameters of the probability distribution of the gene-specific background mutation rate for the gene to increase a fit of the probability distribution to the second number of silent mutations;
        determining, by the computer system, an expected non-silent mutation rate using a sum of context mutation rates of a subset of non-silent mutations in the gene;
        determining, by the computer system, an expected number of samples having at least one non-silent mutation using the expected non-silent mutation rate and the probability distribution of the gene-specific background mutation rate for the gene; and
        comparing, by the computer system, the expected number to a measured number of samples having at least one non-silent mutation to obtain a likelihood value for the measured number; and
    identifying, by the computer system, a group of genes having likelihood values above a threshold as candidate driver genes.

2. The method of claim 1, wherein the one or more parameters of the probability distribution of the gene-specific background mutation rate for the gene include:
    a gene-specific mean of the probability distribution.

3. The method of claim 2, wherein the one or more parameters of the probability distribution of the gene-specific background mutation rate for the gene further include:
    a gene-specific dispersion of the probability distribution.

4. The method of claim 2, wherein:
    the gene-specific mean of the probability distribution is a product of a gene-specific mean coefficient, the expected silent mutation rate for the gene, and the sample mutation rate.

5. The method of claim 4, wherein optimizing the one or more parameters of the probability distribution of the gene-specific background mutation rate for the gene includes:
    using a maximum likelihood estimation of a probability mass function that includes:
        the expected silent mutation rate,
        the second number of silent mutations measured in each of the plurality of samples; and
        the gene-specific mean coefficient, and
    a gene-specific dispersion.

6. The method of claim 5, wherein optimizing the one or more parameters of the probability distribution of the gene-specific background mutation rate for the gene includes:
    maximizing, by the computer system, a posterior probability using a prior probability distribution centered around a previously determined gene-specific mean coefficient and the probability mass function having a fixed value for the gene-specific dispersion, thereby obtaining an updated gene-specific mean coefficient; and
    repeating, by the computer system, the maximum likelihood estimation using the updated gene-specific mean coefficient and the maximizing of the posterior probability until one or more convergence criteria are satisfied.

7. The method of claim 6, wherein maximizing the posterior probability is based on Bayesian inference.

8. The method of claim 6, wherein the previously determined gene-specific mean coefficient is obtained using a regression analysis across the plurality of genes and the plurality of samples using a genome-wide dispersion and a linear combination of known mutation influencing factors that contribute to the gene-specific mean coefficient, wherein the regression analysis optimizes the genome-wide dispersion and linear coefficient of the known mutation influencing factors.

9. The method of claim 8, wherein the regression analysis includes a negative binomial regression.

10. The method of claim 1, further comprising:
    identifying, by the computer system, a group of genes having more non-silent mutations than expected across at least some of the plurality of samples; and
    creating a diagnostic assay to detect mutations of the identified group of genes that are exhibited in the plurality of samples.

11. The method of claim 10, further comprising:
testing a new sample of a new subject using the diagnostic assay to determine whether any of the detected mutations of the identified group of genes exist.

12. The method of claim 11, further comprising:
identifying a treatment for the new subject based on a result of the testing; and
providing the treatment.

13. The method of claim 10, wherein:
the group of genes include a MUC20 gene; and
the diagnostic assay is used for detecting lung cancer.

14. The method of claim 1, where in the probability distribution is a negative binomial distribution, a Poisson distribution, or a beta binomial distribution.

15. The method of claim 1, wherein the subset of non-silent mutations in each of the genes is all of the non-silent mutations in each of the genes.

16. A computer product comprising a computer readable medium storing a plurality of instructions for controlling a sequence analytical system to perform actions comprising:
receiving sequencing data obtained from whole exome sequencing, by the sequence analytical system, of nucleic acid in each sample of a plurality of samples, wherein each sample is from a same tumor type, and wherein the sequence analytical system comprises a sample holder, a detector, and a computer system;
measuring, by the sequence analytical system using the sequencing data, a set of mutations in exons of a plurality of genes in each sample of the plurality of samples, wherein the set of mutations for a subject comprises all mutations detected in the exons of the plurality of genes and provides a total number of mutations measured in the exome of the subject, and wherein the plurality of genes comprises all genes;
for each sample of the plurality of samples, determining, by the computer system, a sample mutation rate based on the total number of mutations measured in the sample;
for each mutation context of a plurality of mutation contexts, determining, by the computer system, a context mutation rate based on a first number of mutations identified in the sets of mutations for the mutation context, wherein a mutation context corresponds to a type of substitution or deletion;
for each gene of the plurality of genes,
determining, for each sample of the plurality of samples, by the computer system, a second number of silent mutations measured in the gene in the sample;
determining, by the computer system, an expected silent mutation rate using a sum of context mutation rates of silent mutations in the gene, wherein a silent mutation does not cause a change to an amino acid sequence of a translated protein for the gene;
determining, by the computer system, a probability distribution of a gene-specific background mutation rate across the plurality of samples for the gene based on the expected silent mutation rate for the gene and the sample mutation rates of the plurality of samples, wherein determining the probability distribution of the gene-specific background mutation rate for the gene includes:
optimizing, by the computer system, one or more parameters of the probability distribution of the gene-specific background mutation rate for the gene to increase a fit of the probability distribution to the second number of silent mutations;
determining, by the computer system, an expected non-silent mutation rate using a sum of context mutation rates of a subset of non-silent mutations in the gene;
determining, by the computer system, an expected number of samples having at least one non-silent mutation using the expected non-silent mutation rate and the probability distribution of the gene-specific background mutation rate for the gene; and
comparing, by the computer system, the expected number to a measured number of samples having at least one non-silent mutation to obtain a likelihood value for the measured number; and
identifying, by the computer system, a group of genes having likelihood values above a threshold as candidate driver genes.

* * * * *